(12) United States Patent
Aferzon

(10) Patent No.: US 9,402,744 B2
(45) Date of Patent: Aug. 2, 2016

(54) PRE-PACKED CORPECTOMY DEVICE TO IMPROVE FUSION

(75) Inventor: Joseph Aferzon, Avon, CT (US)

(73) Assignee: International Spinal Innovations, LLC, West Hartford, CT (US)

( * ) Notice: Subject to any disclaimer, the term of this patent is extended or adjusted under 35 U.S.C. 154(b) by 0 days.

(21) Appl. No.: 12/901,193

(22) Filed: Oct. 8, 2010

(65) Prior Publication Data
US 2011/0307062 A1    Dec. 15, 2011

Related U.S. Application Data

(60) Provisional application No. 61/397,318, filed on Jun. 11, 2010.

(51) Int. Cl.
*A61F 2/44* (2006.01)
*A61F 2/46* (2006.01)
(Continued)

(52) U.S. Cl.
CPC ............... *A61F 2/4611* (2013.01); *A61F 2/44* (2013.01); *A61F 2/4465* (2013.01); *A61F 2/30734* (2013.01); *A61F 2002/2835* (2013.01); *A61F 2002/30551* (2013.01); *A61F 2002/30579* (2013.01); *A61F 2002/30601* (2013.01);
(Continued)

(58) Field of Classification Search
CPC ............ A61F 2002/30551; A61F 2002/30601; A61F 2002/4475; A61F 2002/30734
USPC .......... 623/17.11, 17.12, 17.15, 17.16, 17.13, 623/17.14; 606/90, 105
See application file for complete search history.

(56) References Cited

U.S. PATENT DOCUMENTS 5,236,460 A    8/1993  Barber
5,397,364 A    3/1995  Kozak et al.
(Continued)

FOREIGN PATENT DOCUMENTS

EP    1658830 A1    5/2006
EP    2087857 A1    8/2009
(Continued)

OTHER PUBLICATIONS

International Search Report and Written Opinion issued on Nov. 2, 2011 in International Application No. PCT/US2011/034978.
(Continued)

*Primary Examiner* — Jan Christopher Merene
*Assistant Examiner* — Atiya Mahmud
(74) *Attorney, Agent, or Firm* — Hoffmann & Baron, LLP

(57) ABSTRACT

Corpectomy device comprising outer component, inner component and riser. The outer component includes a first endplate and first structure. The first structure includes a window and seat in communication with the window. The seat defines an opening to be pre-packed substantially with first grafting material. The inner component includes a second endplate and second structure at least partially disposed in the first structure in a first configuration. The second structure is to be pre-packed substantially with second grafting material. The riser has a third tubular structure to be received through the window into the seat to engage at least a portion of the second structure that extends the second structure into a second configuration with respect to the first structure. The third structure is to be pre-packed substantially with third grafting material such that first, second and third grafting material remain pre-packed substantially and in communication in the second configuration.

22 Claims, 13 Drawing Sheets

(51) Int. Cl.
  *A61F 2/30* (2006.01)
  *A61F 2/28* (2006.01)

(52) U.S. Cl.
  CPC ............... *A61F2002/30785* (2013.01); *A61F 2002/30841* (2013.01); *A61F 2002/4475* (2013.01)

(56) References Cited

U.S. PATENT DOCUMENTS

| | | |
|---|---|---|
| 6,066,175 A | 5/2000 | Henderson et al. |
| 6,200,348 B1 | 3/2001 | Biedermann et al. |
| 6,482,233 B1 | 11/2002 | Aebi et al. |
| 6,616,695 B1 | 9/2003 | Crozet et al. |
| 6,866,682 B1 | 3/2005 | An et al. |
| 7,285,134 B2 * | 10/2007 | Berry et al. ............... 623/17.11 |
| 7,544,208 B1 | 6/2009 | Mueller et al. |
| 7,648,529 B2 | 1/2010 | An et al. |
| 7,674,296 B2 | 3/2010 | Rhoda et al. |
| 2004/0153065 A1 | 8/2004 | Lim |
| 2005/0228498 A1 * | 10/2005 | Andres ..................... 623/17.11 |
| 2006/0058880 A1 | 3/2006 | Wysocki et al. |
| 2006/0058881 A1 * | 3/2006 | Trieu ........................ 623/17.16 |
| 2006/0100710 A1 * | 5/2006 | Gutlin et al. ............... 623/17.15 |
| 2006/0129244 A1 * | 6/2006 | Ensign ...................... 623/17.16 |
| 2007/0255408 A1 | 11/2007 | Castleman et al. |
| 2008/0009946 A1 | 1/2008 | Douget et al. |
| 2008/0039948 A1 * | 2/2008 | Biedermann et al. ...... 623/17.16 |
| 2008/0058931 A1 | 3/2008 | White et al. |
| 2008/0114467 A1 * | 5/2008 | Capote et al. ............. 623/23.47 |
| 2009/0138089 A1 * | 5/2009 | Doubler et al. ............ 623/17.16 |
| 2009/0164017 A1 | 6/2009 | Sommerich et al. |
| 2009/0164018 A1 * | 6/2009 | Sommerich et al. ....... 623/17.16 |
| 2009/0204215 A1 * | 8/2009 | McClintock et al. ...... 623/17.11 |
| 2009/0276050 A1 | 11/2009 | Biedermann et al. |
| 2010/0042216 A1 * | 2/2010 | Kilpela et al. ............. 623/17.11 |
| 2010/0249934 A1 * | 9/2010 | Melkent ..................... 623/17.16 |

FOREIGN PATENT DOCUMENTS

| | | |
|---|---|---|
| WO | WO 97/32547 | 9/1997 |
| WO | WO2009/114381 A1 | 9/2009 |
| WO | WO2009/151734 A1 | 12/2009 |

OTHER PUBLICATIONS

European Search Report issued in European Application No. 11792832.5 on Aug. 22, 2013.

* cited by examiner

PRE-PACKED CORPECTOMY DEVICE TO IMPROVE FUSION

CROSS-REFERENCE TO RELATED APPLICATIONS

This application claims priority to and benefit of U.S. Provisional Patent Application Ser. No. 61/397,318, filed on Jun. 11, 2010, which is incorporated herein by reference in its entirety.

BACKGROUND

1. Field of Technology

This application relates generally to spinal fusion. More specifically, this application is directed to a pre-packed corpectomy device and method of bridging vertebrae with the corpectomy device to improve fusion.

2. Brief Description of Related Art

Spinal surgery frequently requires reconstruction of the anterior spinal column. Spinal vertebrae are bony cylindrical structures that are located in front of the spinal cord and nerves; they contribute to the structural support of the axial skeleton. A vertebra can be damaged or destroyed by disease or trauma, resulting in the compression of the spinal cord and/or loss of structural integrity of the spinal column. When the vertebra is removed during spinal surgery to decompress the spinal cord and/or restore structural integrity of the spinal column, it is necessary to reinforce and stabilize the anterior spinal column. A bone graft (e.g., from patient's hip) has traditionally been inserted into a defect site to bridge or fuse the vertebrae above and below the removed vertebra.

While there have been significant efforts to develop artificial weight-bearing devices, the materials that are suitable for the manufacture of these devices do not allow for bone integration. Accordingly, the devices need to have sufficient amount of interior space to pack grafting material, which can facilitate bone integration between the vertebrae. During spinal surgery, a surgical corridor is formed to the defect site, e.g., the diseased or damaged vertebra of the anterior spinal column. The corridor is generally as narrow as possible because there are sensitive and vital structures in front of the anterior spinal column that can be damaged.

To accommodate the materials and the surgical corridor, weight-bearing devices have been designed to have telescoping components that provide vertical expansion from a collapsed state during insertion to an expanded state after insertion into the defect site. Various expansion mechanisms have been designed to facilitate expansion and locking of the telescoping components with respect to one another. Generally, weight-bearing devices that have expansion mechanisms, which are easiest to actuate in the defect site, have the bulkiest exterior dimensions and/or take up the most interior space in the weight-bearing devices, negatively affecting fusion as they do not have sufficient amount of interior space to pack grafting material.

Accordingly, the following characteristics are desirable in an artificial weight-bearing device. It should have proper structural (or weight-bearing) properties. It should have a modulus of elasticity that is close to bone. It should be low profile to facilitate insertion. It should have the ability to expand after insertion into the defect site to accommodate defect sites of various patients. The expansion mechanism should be low profile and easy to actuate. The weight-bearing device should have a sufficient interior space to accommodate grafting material in order to achieve bone integration. It should further facilitate pre-packing of the grafting material before insertion into the defect site. Further, the pre-packed grafting material should be packed tightly after expansion of the device in the defect site.

Currently available artificial weight-bearing devices do not meet the foregoing criteria and require significant improvement. One of the most critical shortcomings is that there is little interior space for pre-packing of grafting material while the device is in a collapsed state. Further, when the device is expanded in the defect site into its expanded state, the grafting material loses its packing inside the interior space of the device. Post-packing the interior space of the device—while the device is expanded in the defect site—is not desirable and presents a danger of dislodging the device or impacting the device into the vertebrae.

SUMMARY

In accordance with an embodiment, a corpectomy device is provided. The corpectomy device includes an outer component, inner component and riser.

The outer component includes a first endplate and first tubular structure that extends from the first endplate. The first tubular structure includes a window that extends around at least a portion of the circumference of the first tubular structure. The first tubular structure further includes a seat above the endplate in communication with the window. The seat defines an opening that is configured to be pre-packed substantially with first grafting material.

The inner component of the corpectomy device includes a second endplate and second tubular structure that extends from the second endplate. The second tubular structure is at least partially disposed in the first tubular structure such that the inner component is in a first telescoping configuration with respect to the outer component. The second tubular structure is configured to be pre-packed substantially with second grafting material.

The riser of the corpectomy device has a third tubular structure that is configured to be received through the window into the seat of the first tubular structure. The third tubular structure engages at least a portion of the second tubular structure to extend and support the inner component with respect to the outer component in a second telescoping configuration. The third tubular structure is configured to be pre-packed substantially with third grafting material.

The first grafting material, second grafting material and third grafting material remain pre-packed substantially and in communication in the second telescoping configuration of the corpectomy device.

In accordance with another embodiment, a corpectomy system is provided. The system includes the corpectomy device described above, an inserter tool and an introducer.

The inserter tool is configured to distract the inner component with respect to the outer component and to allow introduction of the riser into the seat of the outer component. The inserter tool includes a first arm component and second arm that is pivotally connected to the first arm component. The first arm component includes a first extension that is configured to removably engage the outer component and the second arm includes a second extension configured to extend through the outer component to removably engage the inner component.

The inserter tool further includes a first terminal opening, second terminal opening and an insertion surface between the first terminal opening and the second terminal opening, which are configured to communicate the riser through the inserter tool into the seat of the first tubular structure.

The introducer is configured to introduce the riser through the first terminal opening and the second terminal opening via the insertion surface into the seat of the first tubular structure.

In accordance with a further embodiment, a method of bridging vertebrae in a spinal column is provided. The method includes substantially pre-packing a corpectomy device with grafting material, including the outer tubular component, inner tubular component and tubular riser. The inner tubular component is partially disposed inside the outer tubular component. The outer tubular component includes a seat and window.

The pre-packed corpectomy device, including the outer tubular component and inner tubular component, is inserted into the defect site between the vertebrae.

The inner tubular component is distracted with respect to the outer tubular component to open the window such that the window is in communication with the seat of the outer tubular component.

The tubular riser is inserted through the window into the seat of the outer tubular component.

The distraction is removed and allows the vertebrae to apply a load to the corpectomy device such that inner tubular component engages at least a portion of the tubular riser and locks the tubular riser into the seat of the outer tubular component. The tubular riser supports the inner tubular component with respect to the outer component.

The pre-packed grafting material of the outer tubular component, inner tubular component and tubular riser remains pre-packed and in communication when the outer tubular component, inner tubular component and the riser are engaged.

For a more thorough understanding of the present invention, reference is made to the following description, taken in conjunction with the accompanying drawings, and its scope will be pointed out in the appended claims.

BRIEF DESCRIPTION OF THE DRAWINGS

Some embodiments are illustrated by way of example and not limitation in the figures of the accompanying drawings in which.

DETAILED DESCRIPTION

A corpectomy device and method of bridging vertebrae with the corpectomy device to improve fusion are disclosed. In the following description, for the purposes of explanation, numerous specific details are set forth in order to provide a thorough understanding of example embodiments. It will be evident, however, to one skilled in the art, that an example embodiment can be practiced without all of the disclosed specific details.

Figure 1:
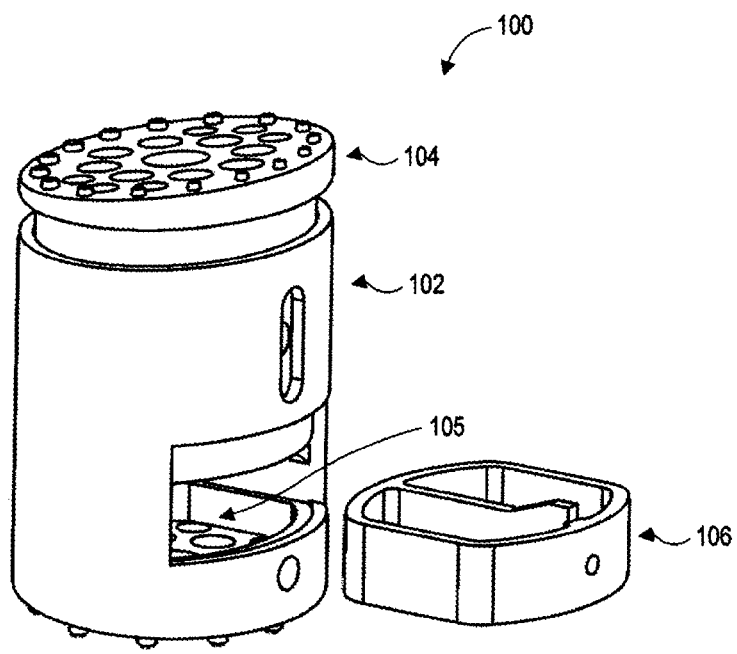
FIG. 1 illustrates a perspective view of an example corpectomy device configured to provide sufficient interior space for pre-packing of grafting material while the device is in a collapsed state and to mitigate the loss of packing when the device is in an expanded state.

FIG. 1 illustrates a perspective view of an example corpectomy device 100 that is configured to provide sufficient interior space for pre-packing of grafting material while the device is in a collapsed state and to mitigate the loss of packing when the device is in the expanded state. The corpectomy device 100 includes an outer component 102, inner component 104, and riser 106. In various embodiments, the corpectomy device 100 described herein is configurable to achieve expansion from the collapsed state to the expanded state of between 10% and 40%, e.g., for differently-dimensioned components 102, 104 and riser 106. Higher expansion between the collapsed and expanded states is feasible.

The corpectomy device 100 and/or components described herein are made of a material, such as a thermoplastic, a polymer, or a composite thereof, which is sufficiently resilient to withstand stress or pressure of bodily movement and positioning, while providing a degree of elasticity and also providing biostablity and biocompatibility. The material should have a modulus of elasticity that is comparable to bone. For example, corpectomy device and/or components thereof may be made of polyetheretherketone (PEEK), a thermoplastic with a Young's modulus of elasticity of about 3.6 GPa and a tensile strength of about 90 MPa. PEEK is practical because it is resistant to both organic and aqueous environments. However, other materials that may be used include metals, ceramics, medical plastics, coral, as well as other medically/surgically applicable materials, and composites thereof.

As will be described in greater detail with reference to the following figures, the upper and lower surfaces (endplates) of the corpectomy device 100 are configured to conform to the shape of the adjacent vertebrae (vertebral endplates) between which the corpectomy device 100 will be implanted in order to approximate and/or restore normal curvature of spine (e.g., lordosis). Further, the endplates of the corpectomy device 100 are sufficiently resilient yet open, providing weight-bearing surfaces that approximate the vertebrae and that enable bridging bone to grow through these surfaces in order to bridge the adjacent vertebrae (e.g., bone fusion).

The outer component 102 is configured to have a generally tubular structure. The tubular structure can have a circular or oval cross-section. In alternate embodiments, the outer component 102 can be configured to have different structures that are designed for particular patients and/or defect sites, such as hexagonal, polygonal, or other structure. A bottom portion of the outer component is capable of being pre-packed substantially with grafting material, as will be described in greater detail herein. The outer component 102 is further configured to mate with the inner component 104 in telescoping configurations, enabling the outer component 102 and inner component 104 to expand/collapse between the collapsed and expanded states. The outer component 104 includes a window 105 to receive the riser 106 to the interior of the outer component 102.

The inner component 104 is also configured to have a generally tubular structure that can mate with the outer component 102 in telescoping configurations, enabling the inner component 104 and outer component 102 to expand/collapse between the collapsed and expanded states. The tubular structure can have a circular or oval cross-section. In alternate embodiments, similarly to the outer component 102, the inner component 104 can also be configured to have different structures (e.g., hexagonal) that are designed for particular patients and/or defect sites. The inner component 104 is capable of being pre-packed substantially with grafting material.

The riser 106 is configured to be received securely into the outer component 102 through the window 105. The riser 106 has a tubular structure which approximates the inner component 104, but which is further truncated to be received through the window 105 into the outer component 102. Similarly to the other components 102, 104, the tubular structure can have an approximately circular or oval cross-section, and can also be varied based on the structure of the other components 102, 104 (e.g., hexagonal or other structure). After receipt into the outer component 102, the riser 106 is further configured to provide weight-bearing support to the inner component 104 and to be locked in the outer component 102 by the inner component 104, mitigating dislodgment of the riser 106 from the corpectomy device 100. Similarly to the inner component 104, the riser 106 is capable of being pre-packed substantially with grafting material.

The grafting material used for pre-packing can include any material that is configured to stimulate bone production through the corpectomy device 100 and fusion of the spinal vertebrae. The material can be harvested (e.g., from the patient or cadaver) or can be artificial (e.g., BPMs and other artificial materials). The grafting material can have a pasty composition (soft and spongy) or can have a more granular, fibrous and/or bony composition. The grafting material should have a consistency, which can be packed (pre-packed) tightly into the corpectomy device 100 and which can retain its shape and position in the corpectomy device during implantation.

In various embodiments, the dimensions of the corpectomy device 100 are approximately the following: the width of the corpectomy device 100 is between about 14 mm and 30 mm; the depth of the corpectomy device 100 is between about 10 mm to about 25 mm; and the height of the corpectomy device is between about 15 mm and about 120 mm. It is noted that the foregoing dimensions are non-limiting and may be appropriately adjusted depending on different levels of the spine (e.g., cervical, lumbar, thoracic) where the corpectomy device 100 is to be implanted, particular patient's spinal anatomy, and/or one or more other factors.

As will be described in greater detail with reference to the following figures, the corpectomy device 100 can be pre-packed substantially with grafting material and implanted into the defect site of the spinal column. Specifically, the corpectomy device 100 (e.g., components 102, 104) in its collapsed state can be inserted into the defect site.

In the defect site, the corpectomy device 100 (e.g., components 102, 104) can be distracted and the riser 106 inserted into the outer component 102. Upon the release of the distraction, the corpectomy device 100 settles into its expanded state with the riser 106 providing weight-bearing support to the inner component 104 and the inner component 104 locking the riser 102 in the outer component 102.

In the expanded state, the corpectomy device 100 (e.g., components 102, 104 and the riser 106) remains packed substantially with grafting material, mitigating the loss of packing in the expanded state experienced in the prior art systems and facilitating improved formation of bridging bone and fusion. Because no post-packing is required while the corpectomy device 100 is in the defect site, the corpectomy device 100 mitigates the possibility of dislodging from or penetrating into the vertebrae of the defect site.

Figure 2:
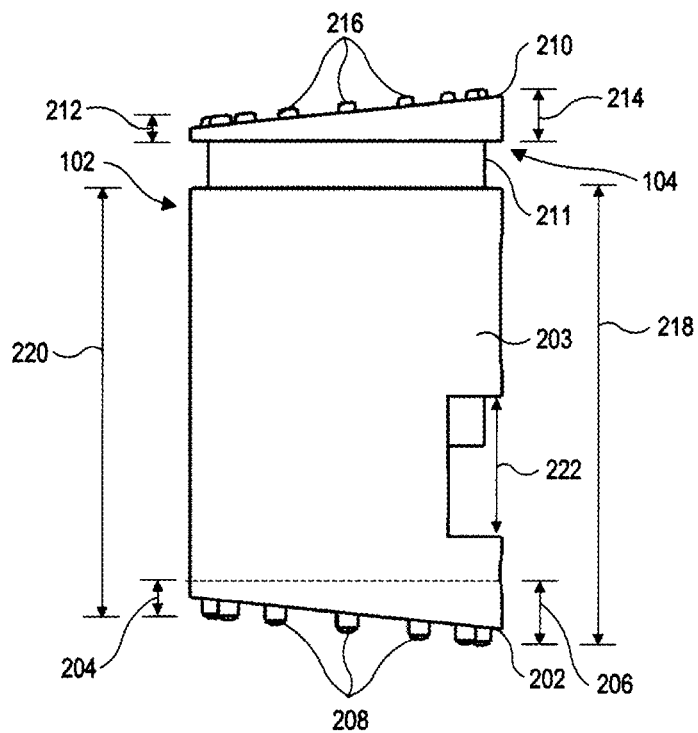
FIG. 2 illustrates a side view of the example corpectomy device illustrated in FIG. 1.

FIG. 2 illustrates a side view of the example corpectomy device 100 illustrated in FIG. 1. The outer component 102 includes a first endplate 202 and first tubular structure 203, and the inner component 104 includes an opposing second endplate 210 and second tubular structure 211. The first endplate 202 has a first height 204 and second opposing height 206, and the endplate 210 also has a first height 212 and second opposing height 214. The degree of triangulation of the endplates 202, 210 can vary for different levels of the spine (e.g., cervical, lumbar, thoracic) and for different patients.

An endplate, such as first endplate 202 or second endplate 210, will generally provide between about a zero (0) and about a six (6) degree angle with respect to a horizontal plane that bisects the corpectomy device 100. Although the combined angle of the endplates 202, 210 can from about zero (0) and up to about twelve (12) degrees, the combined angle will most commonly be between about three (3) and about nine (9) degrees. Other triangulation is possible for certain patients. The triangulation of the endplates 202, 210 provides for the natural curvature of the spinal column at the location into which the corpectomy device 100 will be implanted.

The endplates 202, 210 include attachment devices 208, 116, respectively, configured to penetrate into respective vertebrae in order to anchor the vertebrae and to induce bony ingrowths, integrating or fixating the corpectomy device 100 between vertebrae. The attachment devices 208, 216 can be truncated cone shapes configured to achieve penetration and anchoring. The attachment devices 208, 216 can be disposed in a generally circular or oval arrangement about the periphery of the endplates 202, 210, as will be described in greater detail herein. Other arrangements of the attachment devices 208, 116 about the respective endplates 202, 210 are of course possible.

The attachment devices 208, 216 may be similarly or differently shaped. The shapes of the attachment devices 208, 216 are configured to mitigate movement of the corpectomy device 100 between the vertebrae. The attachment devices 208, 216 can include spikes, keels, flanges and/or other devices that can fixate the corpectomy device 100 to the vertebrae. Still further, the attachment devices 208, 216 can also include certain irregularities about the endplates 202, 210 that increase friction, such as small teeth or ridges running in the same or different directions. The teeth or ridges can be slanted with respect to endplates 202, 210 (e.g., like shark teeth) to better fixate the corpectomy device 100 to the vertebrae.

The outer component 102 has a first (front) height 218 and a second opposing (back) height 220. The tubular structure 203 is generally of a uniform height and does not provide a height differential. Rather, the first height 218 and the second height 220 result from the triangulation of the first endplate 202 described hereinabove. Accordingly, the outer component 102 is taller in the front than in the back, which can provide for the natural curvature of the spine into which the corpectomy device 100 will be implanted. As described herein, the triangulation of the first endplate 202 can vary between about zero (0) and about six (6) degrees.

Figure 11:
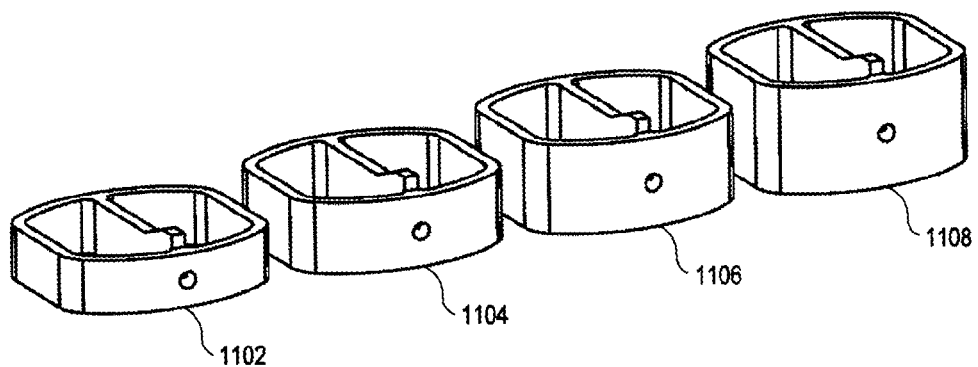
FIG. 11 illustrates example risers that can be received into the outer component through a window of the outer component of FIG. 1.

The window 105 has a height 222 to accommodate risers of different heights described in reference to FIG. 11. In some embodiments, the height 222 is about 10 mm. In other embodiments, the height 222 is between about 3 mm to about 10 mm. In still other embodiments, the height 222 can be greater than 10 mm. Different heights can be selected for the window 105 to accommodate risers of various other/additional heights. Further, the window 105 extends around at least a portion of the circumference of the first tubular structure 203, dimensioned to accommodate the width of the risers described herein.

Figure 3:
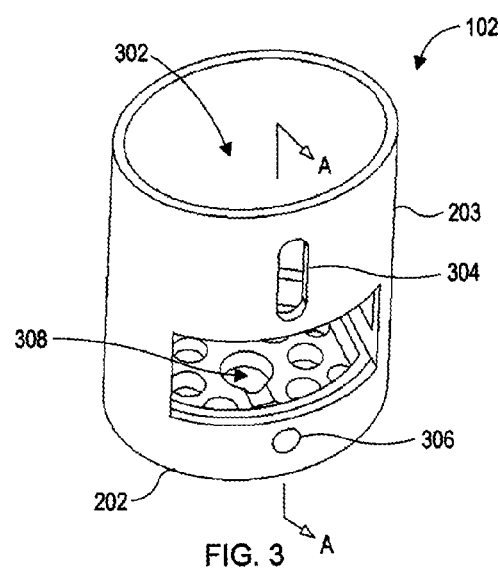
FIG. 3 illustrates a perspective view of the outer component of the corpectomy device illustrated in FIG. 1.

FIG. 3 illustrates a perspective view of the outer component 102 of the corpectomy device 100 illustrated in FIG. 1. The outer component 102 includes openings 302, 304, 306 and 308. Central opening 302 in tubular body 203 is configured to receive the tubular body 211 of the inner component 104 and to facilitate telescoping of the inner component 104 with respect to the outer component 102 between collapsed and expanded states.

Opening 304 is an elongated opening that extends along the height of the outer component 102. Opening 304 is configured to provide access to opening 906 of the inner component 104, which will be described in greater detail below with reference to FIG. 9, such that the outer component 102 can be distracted with respect to the inner component 104 using an inserter tool 2800, which is described with reference to FIGS. 28-30. Opening 306 is configured to removably engage an extension 2906 of the inserter tool 2800, as further described with reference to FIGS. 28-30.

One or more openings 308 extend through the first endplate 202 and are configured to induce bony ingrowths through the openings 308 and to bridge the grafting material pre-packed in the outer component 102 of the corpectomy device 100.

Figure 4:
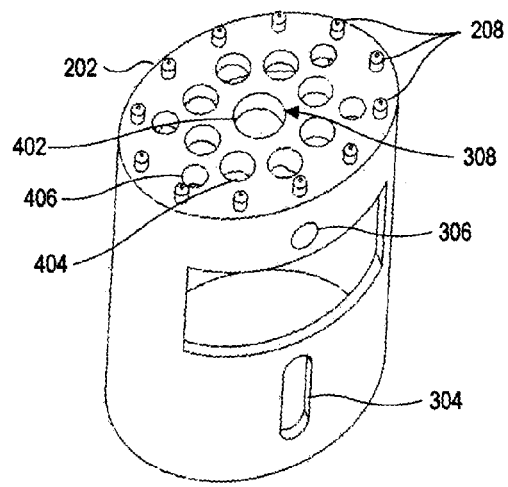
FIG. 4 illustrates a perspective bottom view of the outer component illustrated in FIG. 1.

FIG. 4 illustrates a perspective bottom view of the outer component 100 illustrated in FIG. 1. The attachment devices 208 are disposed about the periphery of the first endplate 202. The openings 308 are disposed generally centrally about the first endplate 202. The locations and number of the openings 308 are designed to retain the substantial weight-bearing capacity of the first endplate 202, while also providing substantial open space to induce bony ingrowths through the openings 308 to the grafting material pre-packed in outer component 102 of the corpectomy device 100. The sizes, patterns and locations of the attachment devices 208 and the openings 308 can be varied for certain locations (defect sites) of the spinal column and/or certain patients. In certain embodiments, the attachment devices 208 can also be interspersed between the openings 308.

In some embodiments as shown in FIG. 4, the openings 308 are disposed in generally circular/oval patterns emanating from about the center of the first endplate 202. The openings 308 can be of the same shape or different shapes (e.g., circular, oval, square, or other another shape) and can have the same or different dimensions. For example, a central opening 402 is circular and has a first diameter, openings 404 are circular and have a second diameter smaller than the first diameter, and openings 406 are circular have a third diameter smaller than the second diameter of openings 404. Further, openings 404 are disposed about the central openings 402, and openings 406 are disposed about the openings 404. Other configurations of openings 308 are of course possible.

Figure 5:
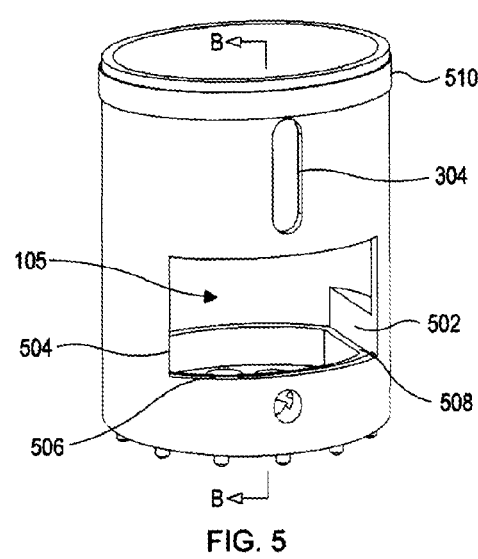
FIG. 5 illustrates a perspective view of the outer component illustrated in FIG. 1.

FIG. 5 illustrates a perspective view of the outer component 102 illustrated in FIG. 1. The internal structure of the outer component 102 includes opposing guide walls 502, 504, ridge 506 and seat 508.

The guide walls 502, 504 are configured to guide the riser 106 into the seat 508. More specifically, the guide walls 502, 504 are sized and dimensioned to approximate the width of the riser 106 and further extend at least partially upward along the interior of the outer component 102. Under operational constraints—when the corpectomy device 100 is under load-bearing conditions within the spinal column—the guide walls 502, 504 provide a backstop to the inner component 104. In various embodiments, the guide walls 502, 504 can extend to different heights and up to the height of the window 105. In some embodiments, the guide walls 502, 504 are of minimal height below the height of the window 105. While it is beneficial to retain as much as possible of the interior space in the outer component 102 for the grafting material, the height of the guide walls 502, 504 can be determined (increased/decreased) based on the height of the riser 106 and the height of the tubular body 211 of the inner component 104 used in the corpectomy device 100.

The seat 508 is recessed with respect to the window 105, forming the ridge 506. The seat 508 is configured to mate in a planar configuration with the riser 106. The guide walls 502, 504 and the ridge 506 are configured to position the riser 106 precisely in the seat 508 of the outer component 102 in order to provide weight-bearing support to the inner component 104 via its tubular body 211. The ridge 506 is further configured to prevent the riser 106 from dislodging out of the outer component 102 through the window 105 and into the defect site.

In some embodiments, at least one reinforcement band 510 can be provided to reinforce the corpectomy device 100, preventing the rupture or failure of the outer component 102. In some circumstances PEEK can fracture or deform (e.g., stress points, possible material deformations). In these and/or other circumstances, reinforcement can be provided to mitigate failure. The reinforcement band 510 can be made of a similar material described in relation to the corpectomy device 100. Reinforcement bands, such as reinforcement band 510, can be disposed at one or more locations of the outer component 102.

More specifically, a band 510 can be provided at a top location as shown in FIG. 5, in a middle location such as between the opening 304 and the window 105, and at a bottom location of the outer component 102 such as between the window 105 and the opening 306. Certain of these or other locations may be indicated based on implantation into certain locations (defect sites) of the spinal column as well as certain patients, which may require additional reinforcement. While guide walls 502, 504 and the seat 508 provide sufficient strength at the bottom of the outer component 102, a band 510 can further be used to provide additional reinforcement to the bottom of the outer component 102, as desired.

Figure 6:
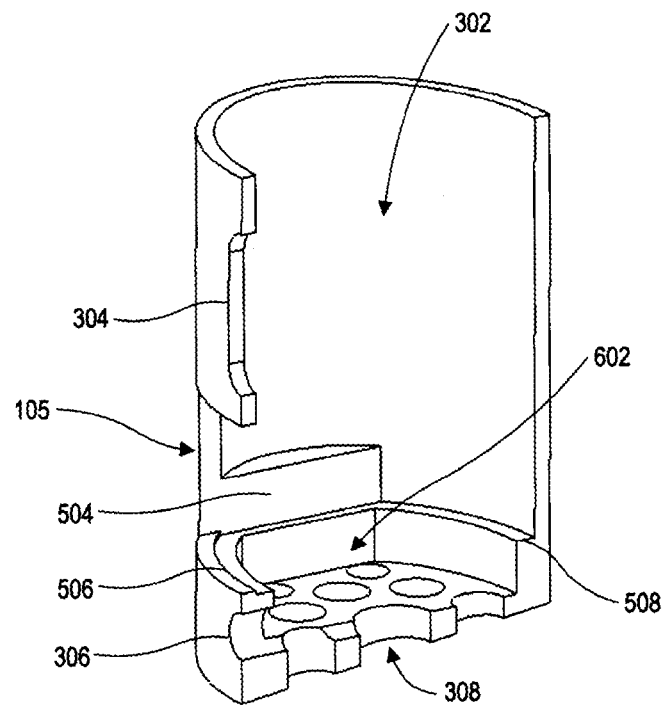
FIG. 6 illustrates a cross-sectional view of the outer component of FIG. 1 along plane B-B shown in FIG. 5.

FIG. 6 illustrates a cross-sectional view of the outer component 100 of FIG. 1 along plane B-B shown in FIG. 5. The seat 508 forms an opening 602, which is in communication with openings 302 and 308. Opening 602 of the outer component 102 will be pre-packed substantially with grafting material to enable bridging bone to be formed through the corpectomy device 100. Specifically, in the expanded state, the grafting material in the outer component 102, inner component 104 and riser 106 will be contiguous to enable bridging bone to be formed through the corpectomy device 100.

Figure 7:
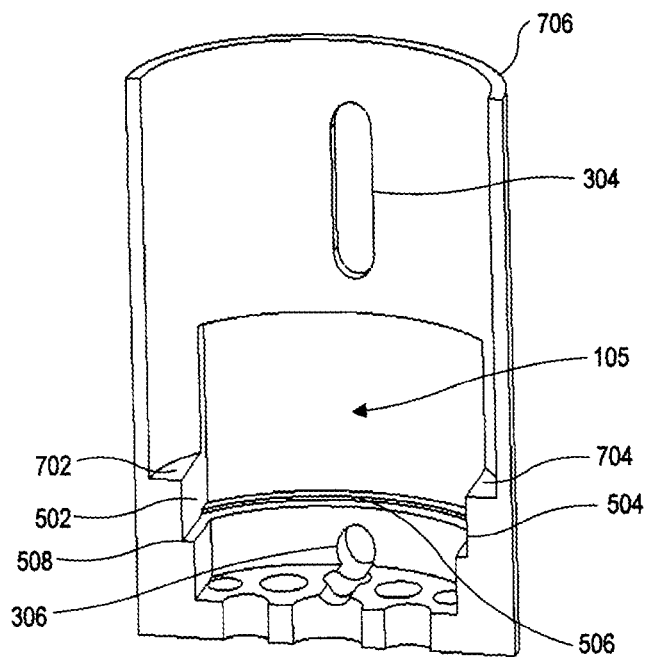
FIG. 7 illustrates a cross-sectional view of the outer component of FIG. 1 along plane A-A shown in FIG. 3.

FIG. 7 illustrates a cross-sectional view of the outer component 102 of FIG. 1 along plane A-A shown in FIG. 3. The guide walls 502, 504 have respective planar surfaces 702, 704 formed by the intersection of the guide walls 502, 504 with the tubular body 203 of the outer component 102. The planar surfaces 702, 704 are configured to provide a backstop to (engage) the tubular body 211 of the inner component 104 in the collapsed state. The tubular body 203 of the outer component 102 further includes a top planar surface 706 configured to further provide a backstop to the second endplate 210 of the inner component 104 in the collapsed state.

Figure 8:
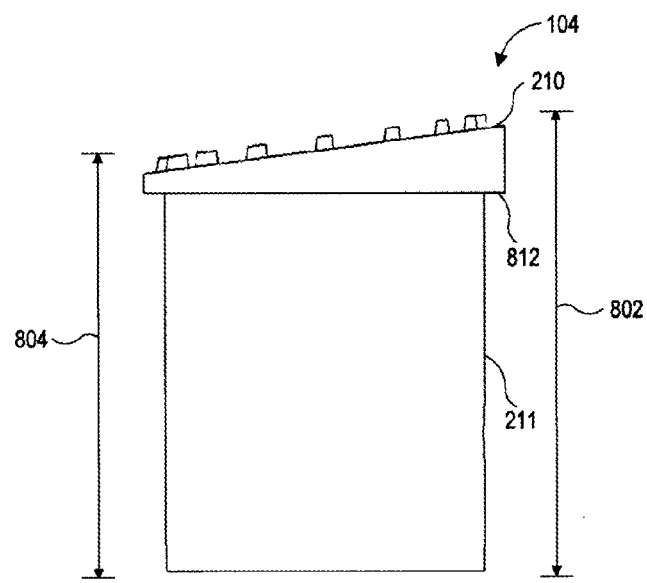
FIG. 8 illustrates a side view of the inner component of the corpectomy device illustrated in FIG. 1.

FIG. 8 illustrates a side view of the example inner component 104 of the corpectomy device 100 illustrated in FIG. 1. The inner component 104 has a first (front) height 802 and a second opposing (back) height 804. The tubular structure 211 is of a generally uniform height and does not provide a height differential. Rather, the first height 802 and the second height 804 result from the triangulation of the second endplate 210 described hereinabove. Accordingly, the inner component 104 is taller in the front than in the back, which can provide for the natural curvature of the spine into which the corpectomy device 100 will be implanted. As described herein, the triangulation of the endplate 210 can vary between about zero (0) and about six degrees (6).

The second endplate 210 is wider than the second tubular structure 211 around at least a portion of the periphery of the inner component 104, creating a lip 812 that can engage the surface 706 of the outer component 102 illustrated in FIG. 7. In some embodiments, the lip 812 extends around the entire periphery of the inner component 104. In other embodiments, the lip 812 extends around the one or more portions of the periphery, such as at the oval portions of the corpectomy device 100. In some other embodiments, the endplate 210 can be the same dimension as the tubular body 211 (similar to the outer component 102), thereby omitting the lip 812.

Figure 9:
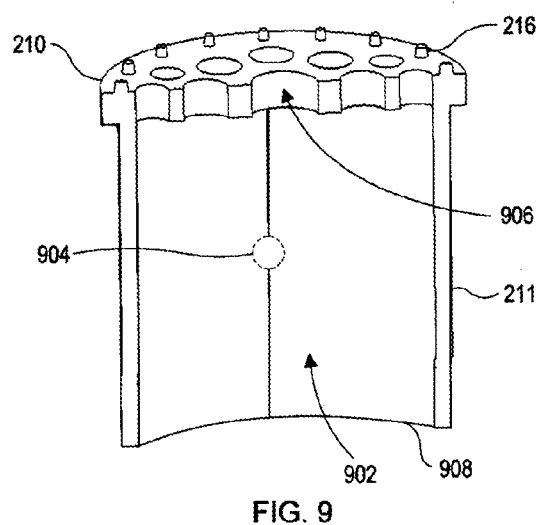
FIG. 9 illustrates a cross-sectional view of the inner component of FIG. 1 along plane C-C shown in FIG. 8.

FIG. 9 illustrates a cross-sectional view of the inner component 104 of FIG. 1 along plane C-C shown in FIG. 8. As described earlier, the inner component 104 includes an endplate 210 and tubular body 211. The inner component 104 further includes openings 902, 904, 906 and a planar surface 908.

Central opening 902 is configured to receive grafting material into the tubular body 211 of the inner component 104. As described earlier, the grafting material is pre-packed into the inner component 104. To facilitate retention of the grafting material pre-packed into the inner component 104, one or more ridges (not shown) can be provided along the central opening of the tubular body 211 (similar to ridges described with reference to the riser 106 in FIG. 12).

Opening 904 is configured to removably engage an extension 2908 of an inserter tool 2800 described below with reference to FIGS. 28-30, such that the outer component 102 can be distracted with respect to the inner component 104. In some embodiments, the opening 904 does not extend through the tubular body 211 of the inner component 104. Under operational constraints—when the corpectomy device 100 is under load-bearing conditions within the spinal column—this mitigates the possibility of grafting material in the inner component 104 from coming out through the opening 904. In other embodiments, the opening 906 extends through the tubular body 211 into the inner component 104.

One or more openings 906 extend through the second endplate 210 and are configured to induce bony ingrowths through the openings 906 and to bridge the grafting material pre-packed in the corpectomy device 100.

As will be described in greater detail below, the planar surface 908 is configured to engage the riser 106, providing structural stability to the corpectomy device 100, such that when the corpectomy device 100 is under operational constraints (load-bearing), sufficient pressure is provided to the pre-packed grafting material to facilitate creation of bridging bone while also providing sufficient rigidity so that the corpectomy device 100 is not crushed or does not fail in the expanded state.

Figure 10:
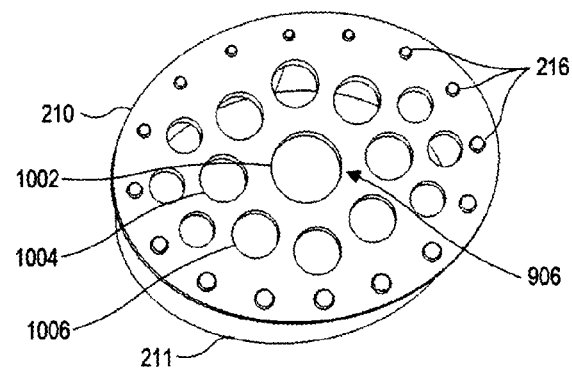
FIG. 10 illustrates an endplate of the inner component of FIG. 1.

FIG. 10 illustrates the endplate 210 of the inner component 104. The attachment devices 216 are disposed about the periphery of the second endplate 210. The openings 906 are disposed generally centrally about the endplate 210. The locations and number of the openings 906 are designed to retain the substantial weight-bearing capacity of the second endplate 210, while also providing substantial open space to induce bony ingrowths through the openings 906 to the grafting material pre-packed in inner component 104 of the corpectomy device 100. The sizes, patterns and locations of the attachment devices 216 and the openings 906 can be varied for certain locations (defect sites) of the spinal column and/or certain patients. In certain embodiments, the attachment devices 216 can also be interspersed between the openings 906.

In some embodiments as shown in FIG. 10, the openings 906 are disposed in generally circular/oval patterns emanating from about the center of the endplate 210. The openings 906 can be of the same shape or different shapes (e.g., circular, oval, square, or other another shape) and can have the same or different dimensions. For example, a central opening 1002 is circular and has a first diameter, openings 1004 are circular and have a second diameter smaller than the first diameter, and openings 1006 are circular have a third diameter smaller than the second diameter of openings 1004. Further, openings 1004 are disposed about the central openings 1002, and openings 1006 are disposed about the openings 1004. Other configurations of openings 906 are of course possible.

FIG. 11 illustrates example risers 1102-1108 that can be received into the outer component 102 through the window 105. The example riser 106 of FIG. 1 can be any one of the example risers 1102-1108. The risers 1102-1108 are graduated in height from about 3 mm for riser 1102 to about 10 mm or greater for riser 1108. In some embodiments, the height-increments between the risers can be about 1 mm, while in other embodiments, the height-increments can be about 2 mm, or greater. Other intermediate or fractional height increments are of course possible. The height of the corpectomy device 100 in the expanded state can be configurable based on the height of the riser 106 (e.g., risers 1102-1108) that is used in the corpectomy device 100. Accordingly, the corpectomy device 100 can be correctly sized for certain defect sites in the spinal column and for certain patients.

Figure 12:
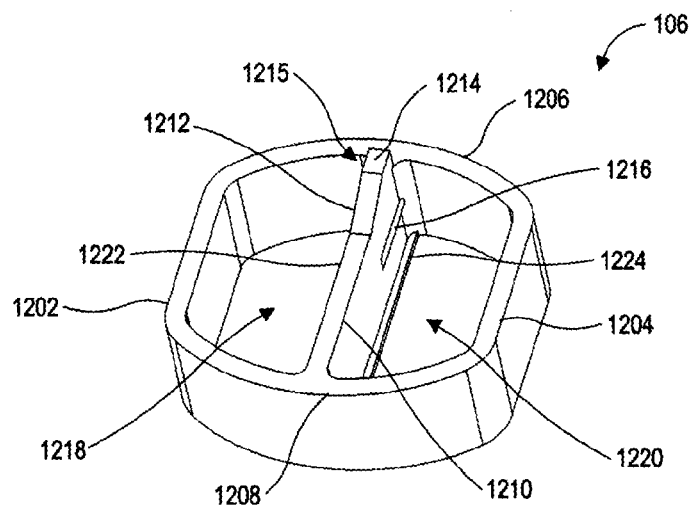
FIG. 12 illustrates the riser of FIG. 1 in greater detail.

FIG. 12 illustrates the example riser 106 of FIG. 1 in greater detail. The riser 106 includes opposing sidewalls 1202, 1204, opposing accurate walls 1206, 1208, middle wall 1210 and locking mechanism 1215.

The configuration of the riser 106 approximates the configuration of the tubular body 211 of the inner component 104 (e.g., circular/oval configuration), which is truncated to create opposing sidewalls 1202, 1204 that are dimensioned to fit the window 105 and to be guided by guide walls 502, 504 into the seat 508 of the outer component 102.

Opposing accurate walls 1206, 1208 are configured to engage the planar surface 908 of the tubular body 211 of the inner component 104, providing structural stability to the corpectomy device 100 under operational constraints (load-bearing).

The middle wall 1210 is configured to provide structural stability to the riser 106, sectioning the riser 106 into openings 1220 and 1222 that can be pre-packed with grafting material. The middle wall includes an opening 1216, locking mechanism 1215 and retention ridges 1222, 1224.

The opening 1216 is configured to removably engage an extension of an introducer tool 3002, as will be described in greater detail with reference to FIG. 30. The opening 1216 extends through arcuate wall 1206 and partially into the middle wall 1210.

The locking mechanism 1215 is configured to facilitate insertion of the riser 106 into the outer component 102 and to secure the riser 106 in the seat 508 of the outer component 102 by engaging the tubular body 211 of the inner component 104. The locking mechanism 1215 includes a sloped surface 1212 and planar surface 1214. During insertion, the tubular body 211 of the inner component 104 can ride or traverse along the middle wall 1210, up the sloped surface 1212, levelling off along planar surface 1214, and finally locking into place via the locking mechanism 1215 along accurate wall 1206.

In some embodiments, the middle wall 1210 can be omitted entirely. For example, the ridge 506 can retain the riser 106 in the seat 508 of the outer component 102 via pressure from the inner component 104 under load-bearing conditions. In other embodiments, the middle wall 1210 can be omitted partially, with the locking mechanism 1215 remaining.

The retention ridges 1222, 1224 can be provided along the bottom of the middle wall 1210 to help retain grafting material pre-packed in the respective openings 1218, 1220. In other embodiments, the retention ridges 1222, 1224 can additionally or alternatively be provided along the bottom of the walls 1202, 1204. In some embodiments, the retention ridges 1222, 1224 can be omitted, while still in other embodiments, the retention ridges 1222, 1224 can extend around the interior of the openings 1218, 1220.

Figure 13:
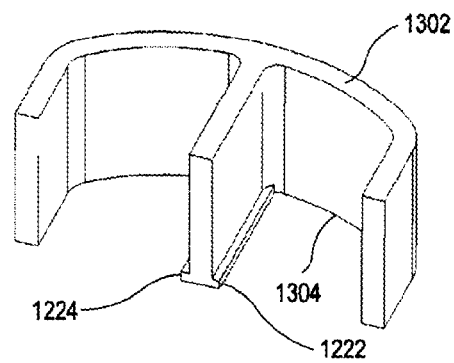
FIG. 13 illustrates cross-sectional view of the riser of FIG. 1.

FIG. 13 illustrates cross-sectional view of the example riser 106. The riser 106 includes a top surface 1302 and a bottom surface 1304. The top surface 1302 engages the planar surface 908 of the tubular body 211 of the inner component 104, while the bottom surface 1304 engages the seat 508 of the outer component 102. The example riser 106 provides weight-bearing support for the inner component 104 against the outer component 102, as well as for pre-packing of grafting material to facilitate bone formation through the corpectomy device 100.

Figure 14:
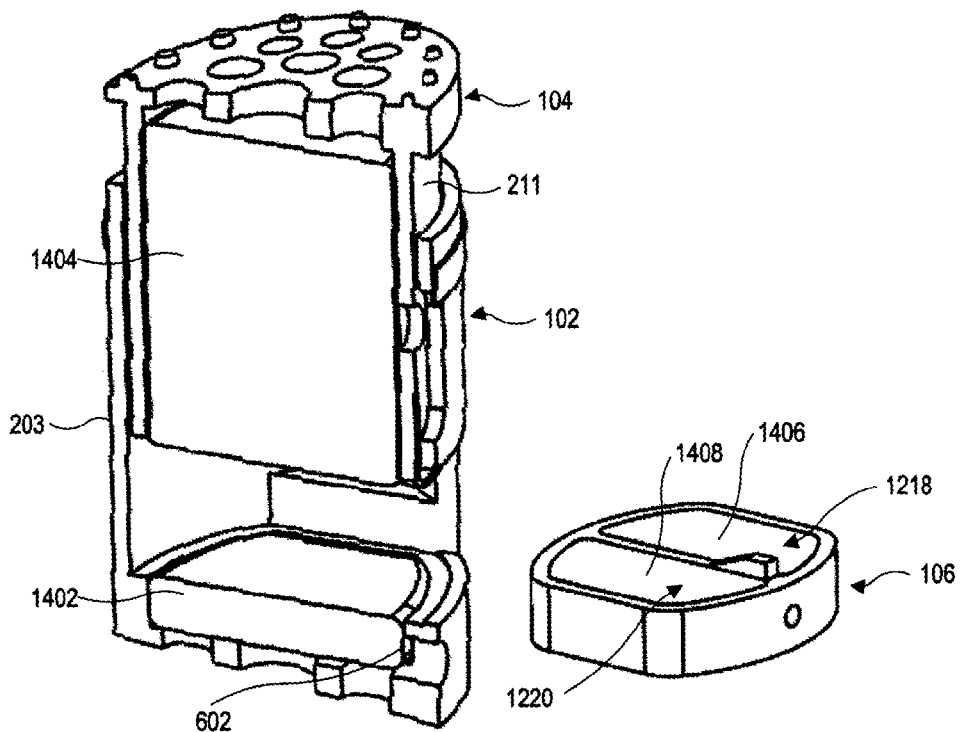
FIG. 14 illustrates a cross-sectional view of the corpectomy device of FIG. 1 pre-packed with grafting material.

FIG. 14 illustrates a cross-sectional view of an example corpectomy device 100 of FIG. 1 that is pre-packed with grafting material. The corpectomy device 100 has been expanded slightly from its collapsed state to illustrate the pre-packing of the corpectomy device 100 in greater detail.

As illustrated, opening 602 of the outer component 102 is pre-packed with grafting material 1402. The entire tubular body 211 of the inner component 104 is pre-packed with grafting material 1404. Openings 1218, 1220 of the riser 106 are pre-packed with respective grafting material 1406, 1408.

It is noted, however, that the pre-packed corpectomy device 100 in its collapsed state (inner component 104 fully inserted into outer component 102) is implanted into the defect site of the spinal column, then distracted sufficiently to receive the pre-packed riser 106 into the outer component 102, and locked in its expanded state by the inner component 104 engaging the riser 106 as the distraction is released.

FIGS. 15-18 illustrate cross-sectional views of the corpectomy device 100 to show in greater detail the insertion of the riser 106 into the outer component 102 to extend the corpectomy device 100 from the collapsed state into the expanded state. For purposes of clear illustration, the grafting material 1402-1408 of the respective components 102-106 in the corpectomy device 100 has been removed. It is noted, however, that a pre-packed corpectomy device 100 illustrated in FIG. 14 will be used for spinal fusion procedures.

At this point it is assumed that the pre-packed components 102, 104 of the corpectomy device 100 in a collapsed state have been inserted into proper positions in the defect site of the spinal column, with the endplates 202, 210 of the components 102, 104 contacting but not yet engaging the vertebrae of the defect site via respective attachment devices 208, 216.

Figure 15:
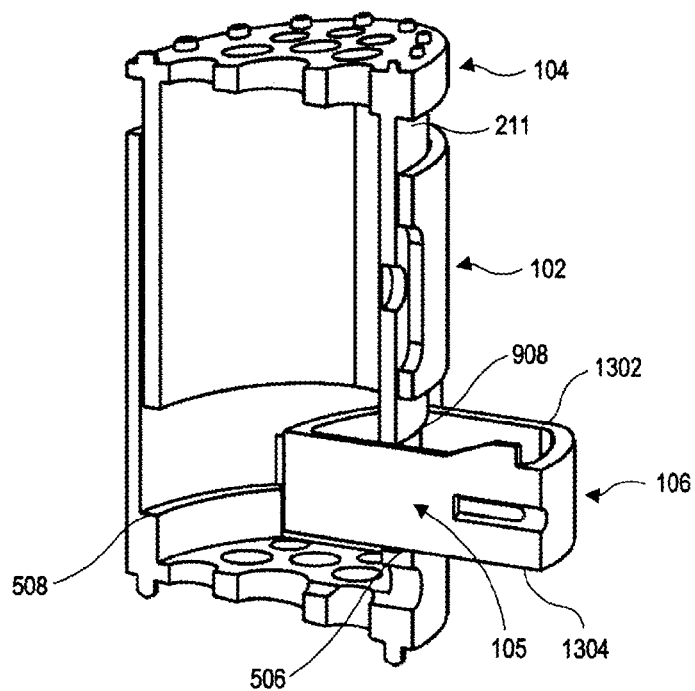
FIGS. 15-18 illustrate cross-sectional views of the corpectomy device of FIG. 1 to show the insertion of the riser into the outer component to extend the corpectomy device from the collapsed configuration into the expanded configuration.

As illustrated in FIG. 15, the inner component 104 has been distracted sufficiently with respect to outer component 102 from the collapsed state to open at least a portion of the window 105 in the outer component 102 in order to receive the riser 106. In this state, the attachment devices 208, 216 of the respective endplates 202, 210 in the components 102, 104 engage the vertebrae of the defect site. The riser 106 is inserted through the window 105 into the seat 508 of the component 102. To facilitate insertion of the riser 106, the surface 908 of the tubular body 211 of the inner component 104 can ride the top surface 1302 of the riser 106. Similarly, the ridge 506 and seat 508 can ride the bottom surface 1304 of the riser 106.

Figure 16:
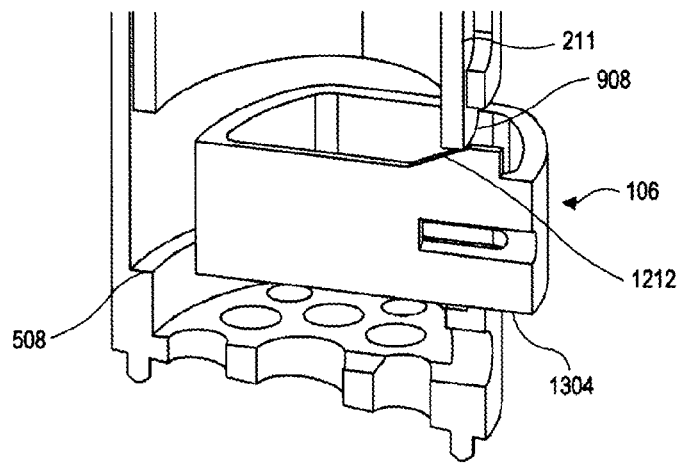

As illustrated in FIG. 16, the inner component 104 can further be distracted with respect to outer component 102 such that the surface 908 of the tubular body 211 of the inner component 104 rides up sloped surface 1212 of the riser 106 as the riser 106 is inserted into the seat 508 of the outer component 102.

Figure 17:
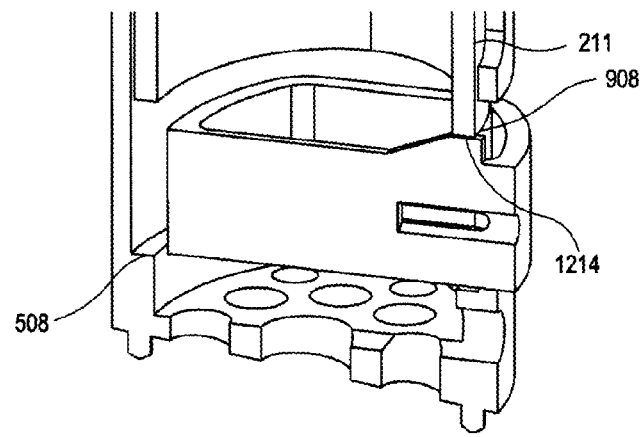

As illustrated in FIG. 17, the surface 908 of the tubular body 211 of the inner component 104 levels off on surface 1214 of the riser 106 as the riser 106 is inserted farther into the seat 508 of the outer component 102.

Figure 18:
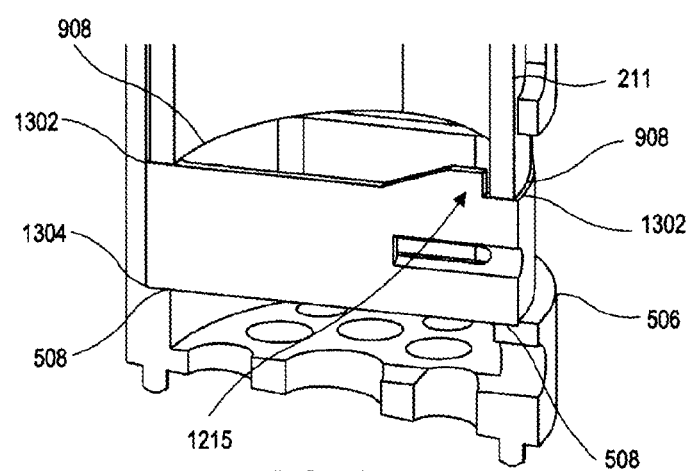

As further illustrated in FIG. 18, when the locking mechanism 1215 clears the surface 908 of the tubular body 211 of the inner component 104, the distraction with respect to components 102, 104 is released. As the distraction is released, the vertebrae of the defect site apply a load to the corpectomy device 100. The surface 908 of the inner component 104 engages the top surface 1302 of the riser 106 (of walls 1206 and 1208) and the seat 508 of outer component 102 engages the bottom surface 1304 (of walls 1202, 1204, 1206 and 1208) of the riser 106. Accordingly, the riser 106 is locked via the ridge 506 and lock 1215 in the seat 508 of the outer component 102 by the inner component 104.

As shown illustrated in and described with reference to FIGS. 15-18, the corpectomy device 100 has been extended from a collapsed state (insertion state) into an expanded state (operational state). In the expanded state, the attachment devices 208, 216 of the respective endplates 202, 210 in the components 102, 104 continue to engage the vertebrae of the defect site.

In the expanded state, the corpectomy device 100 is under operational or load-bearing conditions within the defect site of the spinal column. The engagement of the respective components 102, 104, 106 causes their pre-packed grafting material 1402-1408 to be in communication throughout the corpectomy device 100. Further, the pressure generated by the vertebrae (e.g., via ligaments, muscles) on the corpectomy device 100 pressurizes the pre-packed grafting material 1402-1408 throughout the corpectomy device 100. The communication and pressurization of the pre-packed grafting material 1402-1408 improves formation of the bridging bone though the corpectomy device 100 and to the vertebrae of the defect site.

Figure 19:
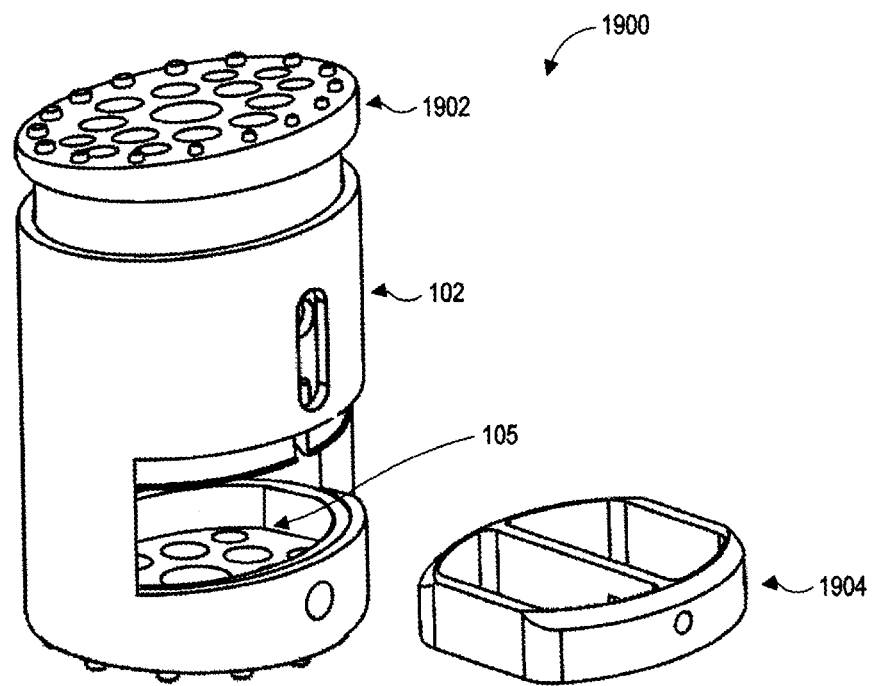
FIG. 19 illustrates a perspective view of another example corpectomy device that is configured to provide sufficient interior space for pre-packing of grafting material while the device is in a collapsed state and to mitigate the loss of packing when the device is in the expanded state.

FIG. 19 illustrates a perspective view of another example corpectomy device 1900 that is configured to provide sufficient interior space for pre-packing of grafting material while the device is in a collapsed state and to mitigate the loss of packing when the device is in the expanded state. The corpectomy device 1900 includes an outer component 102, inner component 1902, and riser 1904. In various embodiments, the corpectomy device 1900 described herein is configurable to achieve expansion from the collapsed state to the expanded state of between about 10% to about 40%, e.g., for differently-dimensioned components 102, 1902 and riser 1904. Higher expansion between the collapsed and expanded states is feasible.

The corpectomy device 1900 and/or components described herein are made of similar materials described above with reference to the corpectomy device 100, which are sufficiently resilient to withstand stress or pressure of bodily movement and positioning, while providing a degree of elasticity and providing biostablity and biocompatibility. The materials may be used include a thermoplastic (e.g., PEEK), polymer, medical plastic, coral, metal, ceramic, as well any other medically/surgically applicable material, and composites thereof.

The upper and lower surfaces (endplates) of the corpectomy device 1900 are configured to conform to the shape of the vertebrae (vertebral endplates) between which the corpectomy device 1900 will be implanted in order to approximate and/or restore normal curvature of spine (e.g., lordosis). Further, the endplates of the corpectomy device 1900 are sufficiently resilient yet open, providing weight-bearing surfaces that approximate the vertebrae and that enable bridging bone to grow through these surfaces in order to bridge the adjacent vertebrae (e.g., bone fusion).

The structure of the outer component 102 has been described in greater detail with reference to FIGS. 1-7. Generally, the outer component 102 has a tubular structure (e.g., circular, oval, hexagonal, polygonal or other cross-section) and at least a portion (bottom opening 602) of the outer component 102 can be pre-packed substantially with grafting material. The outer component 102 is configured to mate with the inner component 1902 in telescoping configurations, enabling the outer component 102 and inner component 1902 to expand/collapse between the collapsed and expanded states. The window 105 of the outer component 102 receives a riser 1904 to the interior of the outer component 102.

The inner component 1902 is also configured to have a generally tubular structure (e.g., circular, oval, hexagonal, polygonal or other cross-section) that can mate with the outer component 102 in telescoping configurations, enabling the inner component 1902 and outer component 102 to expand and collapse between the collapsed and expanded states. The inner component 1902 can be pre-packed substantially with grafting material. In alternate embodiments, components 102, 1902 can also be configured to have different structures that are designed for particular patients and/or defect sites.

The riser 1904 is configured to be received securely into the outer component 102 through the window 105. The riser 1904 can have a height described herein with reference to FIG. 11, or can have a different height. The riser 1904 has a tubular structure (e.g., circular, oval, hexagonal, polygonal or other cross-section), which approximates the inner component 1902, but which is truncated to be received through the window 105 into the outer component 102. Similarly to the other components 102, 1902, the structure of the riser 1904 can also be varied based on the structure of the other components 102, 1902. After receipt into the outer component 102, the riser 1904 is further configured to provide weight-bearing support to the inner component 1902 and to be locked in the outer component 102 by the inner component 1902, mitigating dislodgment of the riser 1904 from the corpectomy device 1900. Similarly to the inner component 1902, the riser 1904 can be pre-packed substantially with grafting material.

In various embodiments, the dimensions of the corpectomy device 1900 can be similar to or different than the dimensions of the corpectomy device 100 described herein. These dimensions are non-limiting and may be appropriately adjusted depending on different levels of the spine (e.g., cervical, lumbar, thoracic) where the corpectomy device 1900 is to be implanted, particular patient's spinal anatomy, and/or one or more other factors.

As will be described in greater detail with reference to the following figures, the corpectomy device 1900 can be pre-packed substantially with grafting material and implanted into a defect site of a spinal column. Specifically, the corpectomy device 1900 (e.g., components 102, 1902) in its collapsed state is inserted into the defect site.

In the defect site, the corpectomy device 1900 (e.g., components 102, 1902) can be distracted and the riser 1904 inserted into the outer component 102. Upon the release of the distraction, the corpectomy device 1900 settles into its expanded state with the riser 1904 providing weight-bearing support to the inner component 1902 and the inner component 1902 locking the riser 1904 in the outer component 102.

In the expanded state, the corpectomy device 1900 (e.g., components 102, 1902 and the riser 106) remains packed substantially with grafting material, mitigating the loss of packing in the expanded state experienced in the prior art systems and facilitating improved formation of bridging bone and fusion. Because no post-packing is required while the corpectomy device 1900 is in the defect site, the corpectomy device 1900 mitigates the possibility of dislodging from or penetrating into the vertebrae of the defect site.

Figure 20:
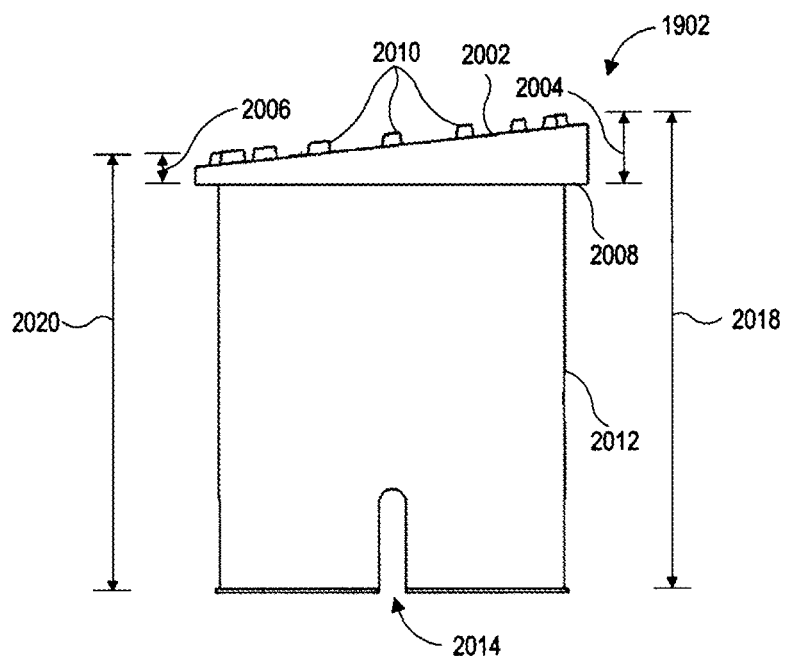
FIG. 20 illustrates a side view of the inner component of the corpectomy device illustrated in FIG. 19.

FIG. 20 illustrates a side view of the example inner component 1902 of the corpectomy device 1900 illustrated in FIG. 19. The inner component 1902 has a first (front) height 2018 and a second opposing (back) height 2020. The inner component 1902 includes a second endplate 2002 and second tubular body 2012. The second endplate 2002 has a first (front) height 2004 and a second opposing (back) height 2006. Accordingly, the inner component 1902 is taller in the front than in the back, which provides for the natural curvature of the spine into which the corpectomy device 1900 will be implanted.

The tubular structure 2012 is of a generally uniform height and does not provide a height differential 2018, 2020. Rather, the first height 2004 and the second height 2006 result from the triangulation of the second endplate 2002 as described below in greater detail.

The second endplate 2002 is wider than the second tubular structure 2012 around at least a portion of the periphery of the inner component 1902, creating a lip 2008 that can engage surface 706 of the outer component 102. Lip 2008 can be similar to or different than the lip 812 of the inner component 104, as described with reference to FIG. 8.

Although the first endplate 202 is described with reference to FIGS. 1-7, the degree of triangulation of the endplates 202, 2002 can vary for different levels of the spine (e.g., cervical, lumbar, thoracic) and for different patients. An endplate, such as the first endplate 202 or second endplate 2002, will generally provide between about a zero (0) and about a six (6) degree angle with respect to a horizontal plane that bisects the corpectomy device 1900. Although the combined angle of the endplates 202, 2002 can vary from about zero (0) and up to about twelve (12) degrees, the combined angle will most commonly be between about three (3) and about nine (9) degrees. Other triangulation is possible for certain patients. The triangulation of the endplates 202, 2002 provides for the natural curvature of the spinal column at the location into which the corpectomy device 1900 will be implanted.

The endplates 202, 2002 include attachment devices 208, 2010 configured to penetrate into respective vertebrae in order to anchor the vertebrae and to induce bony ingrowths, integrating or fixating the corpectomy device 1900 between vertebrae. The attachment devices 208 of the first endplate 202 were described with reference to outer component 102 of FIGS. 1-7. The attachment devices 2010 of the second endplate 2002 can be similar to or different than the attachment devices 216 of the second endplate 210 described hereinabove with reference to FIG. 10. The alternative types of attachment devices described above with reference to the attachment devices 216 are applicable with respect to the attachment devices 2010. The attachment devices 2010 can be disposed in a generally circular or oval arrangement about the periphery of the endplate 2002. Other arrangements of the attachment devices 2010 about the endplate 2002 are of course possible.

The tubular body 2012 of the inner component 1902 includes a locking mechanism 2014 configured to facilitate insertion of the riser 1904 into the outer component 102 and to secure the riser 1904 in the seat 508 by engaging the locking mechanism 2014 against the riser 1904 and the outer component 102. The locking mechanism 2014 will be described in greater detail below with reference to FIG. 21.

Figure 21:
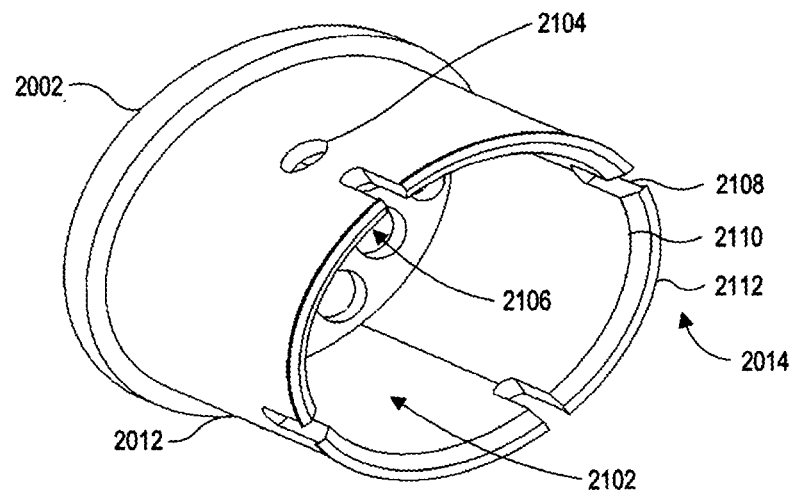
FIG. 21 illustrates a perspective bottom view of the inner component illustrated in FIG. 19.

FIG. 21 illustrates a perspective bottom view of the inner component 1902 illustrated in FIG. 19. The inner component 1902 includes openings 2102, 2104, 2106 and locking mechanism 2014.

Central opening 2102 is configured to receive grafting material into the tubular body 2012 of the inner component 1902. As described herein, grafting material is pre-packed into the inner component 1902.

Opening 2104 is configured to removably engage an extension 2906 of an inserter tool 2800 described below with reference to FIGS. 28-30, such that the outer component 102 can be distracted with respect to the inner component 1902. In some embodiments, the opening 2104 does not extend through the tubular body 2012 of the inner component 1902. Under operational constraints—when the corpectomy device 1900 is under load-bearing conditions within the spinal column—this mitigates the possibility of grafting material in the inner component 1902 from coming out through the opening 2104. In other embodiments, the opening 2104 extends through the tubular body 2012 into the inner component 1902.

One or more openings 2106 extend through the endplate 2002 and are configured to induce bony ingrowths through the openings 2106 and to bridge the grafting material pre-packed in the inner component 1902 of the corpectomy device 1900.

The locking mechanism 2014 includes one or more expansion slots 2108, chamfered surface 2110, and engagement member 2112. As will be described in greater detail with reference to FIG. 28, the chamfered surface 2110 is configured to engage the riser 1904 such that when the corpectomy device 1900 is under operational constraints (load-bearing), the expansion slots 2108 allow the tubular body 2012 to expand circumferentially, engaging the engagement member 2112 against the outer component 102.

Figure 22:
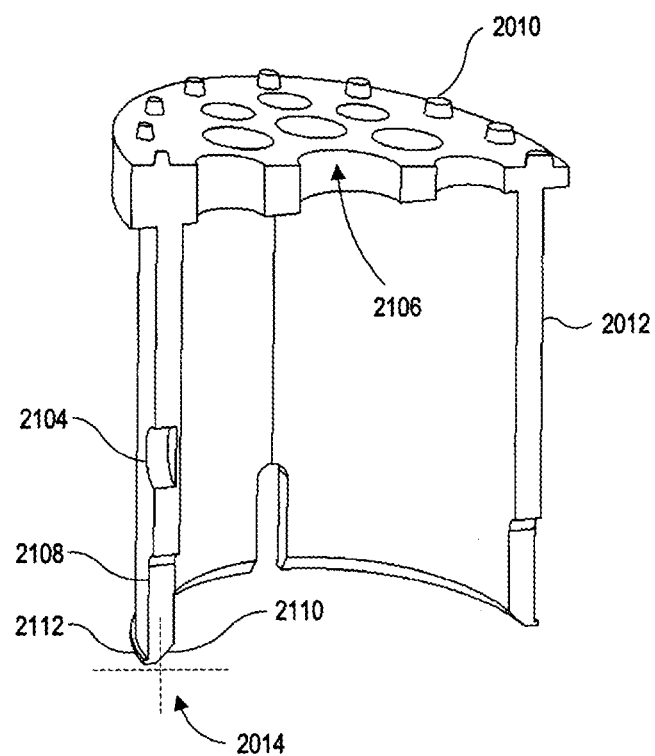
FIG. 22 illustrates a locking mechanism of FIG. 21 in greater detail.

FIG. 22 illustrates the locking mechanism of FIG. 21 in greater detail. The engagement member 2112 extends about at least a portion of the circumference of the tubular body 2012. The engagement member 2012 is generally planar and intersects the chamfered surface 2110 approximately midway along the thickness of the tubular body 2012, as shown by the dashed lines. Other configurations of the chamfered surface 2110 and the engagement member 2012 are of course possible.

Figure 23:
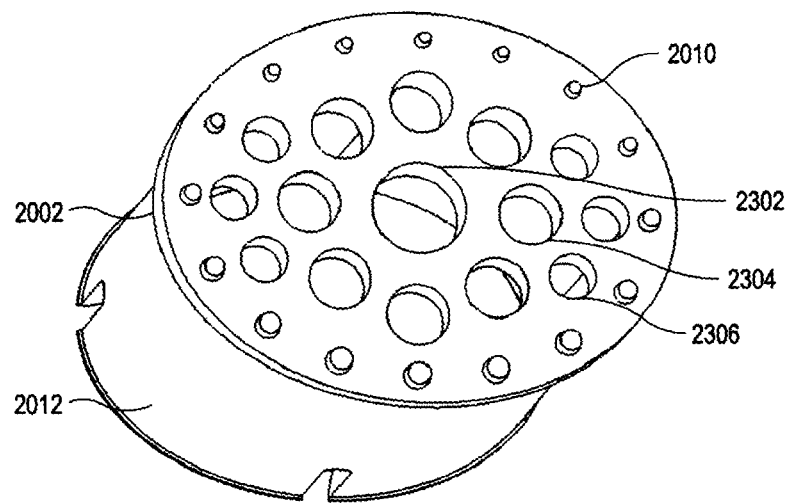
FIG. 23 illustrates the endplate of the inner component of FIG. 19.

FIG. 23 illustrates endplate 2002 of the inner component 1902. The attachment devices 2010 are disposed about the periphery of the endplate 2002. The openings 2106 are disposed generally centrally about the endplate 2002. The locations and number of the openings 2106 are designed to retain the substantial weight-bearing capacity of the endplate 2002, while also providing substantial open space to induce bony ingrowths through the openings 2106 to the grafting material pre-packed in inner component 1902 of the corpectomy device 1900. The sizes, patterns and locations of the attachment devices 2010 and the openings 2106 can be varied for certain locations (defect sites) of the spinal column and/or certain patients. In certain embodiments, the attachment devices 2106 can also be interspersed between the openings 2106.

In some embodiments as shown in FIG. 23, the openings 2106 are disposed in generally circular/oval patterns emanating from about the center of the endplate 2002. The openings 2106 can be of the same shape or different shapes (e.g., circular, oval, square, or other another shape) and can have the same or different dimensions. For example, a central opening 2302 is circular and has a first diameter, openings 2304 are circular and have a second diameter smaller than the first diameter, and openings 2306 are circular have a third diameter smaller than the second diameter of openings 2304. Further, openings 2304 are disposed about the central openings 2302, and openings 2306 are disposed about the openings 2304. Other configurations of the openings 2106 are of course possible.

Figure 24:
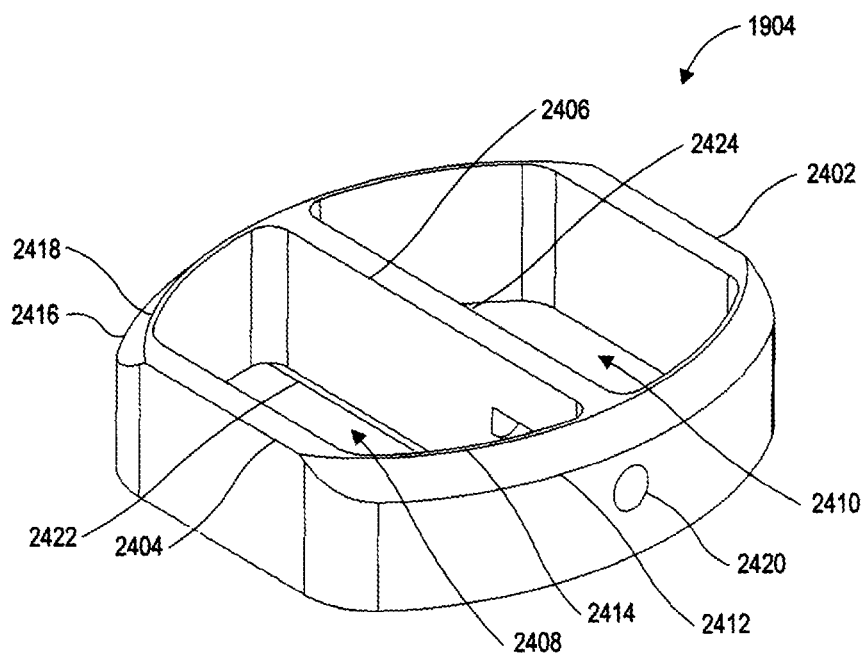
FIG. 24 illustrates the example riser of FIG. 19 in greater detail.

FIG. 24 illustrates the example riser 1904 of FIG. 19 in greater detail. The riser 1904 is generally similar to risers of FIGS. 1, 11 and 12, except as described hereinbelow. The riser 1904 includes opposing sidewalls 2402, 2404, middle wall 2406 and opposing accurate walls 2412, 2416.

The configuration of the riser 1904 approximates the configuration of the tubular body 2012 of the inner component 1902 (e.g., circular/oval configuration), which is truncated to create the opposing sidewalls 2402, 2404 that are sized and dimensioned to fit the window 105 and to be guided by the guide walls 502, 504 into the seat 508 of the outer component 102.

The middle wall 2406 is configured to provide structural stability to the riser 1904, sectioning the riser 1904 into openings 2408 and 2410 that can be pre-packed with grafting material. The middle wall includes an opening 2420 and retention ridges 2422, 2424.

The opening 2420 is configured to removably engage an extension of an introducer tool 3002, as will be described in greater detail with reference to FIG. 30. The opening 2420 extends through arcuate wall 2412 and partially into the middle wall 2406.

Opposing accurate walls 2412, 2416 include respective sloped surfaces 2414, 2418. The accurate walls 2412, 2416 are configured to engage (via sloped surfaces 2414, 2418) the chamfered surface 2110 of the tubular body 2012 of the inner component 1902, providing structural stability to the corpectomy device 1900 and locking the components of the corpectomy device 1900 (102, 1902, 1904) in respect to one another under operational constraints (load-bearing).

The retention ridges 2422, 2424 can be provided along the bottom of the middle wall 2406 to help retain grafting material pre-packed in the respective openings 2408, 2410. In other embodiments, the retention ridges 2422, 2424 can be additionally or alternatively provided along the bottom of the walls 2402, 2404. In some embodiments, the retention ridges 2422, 2424 are omitted, while still in other embodiments, the retention ridges 2422, 2424 extend around the interior of the openings 2408, 2410.

Figure 25:
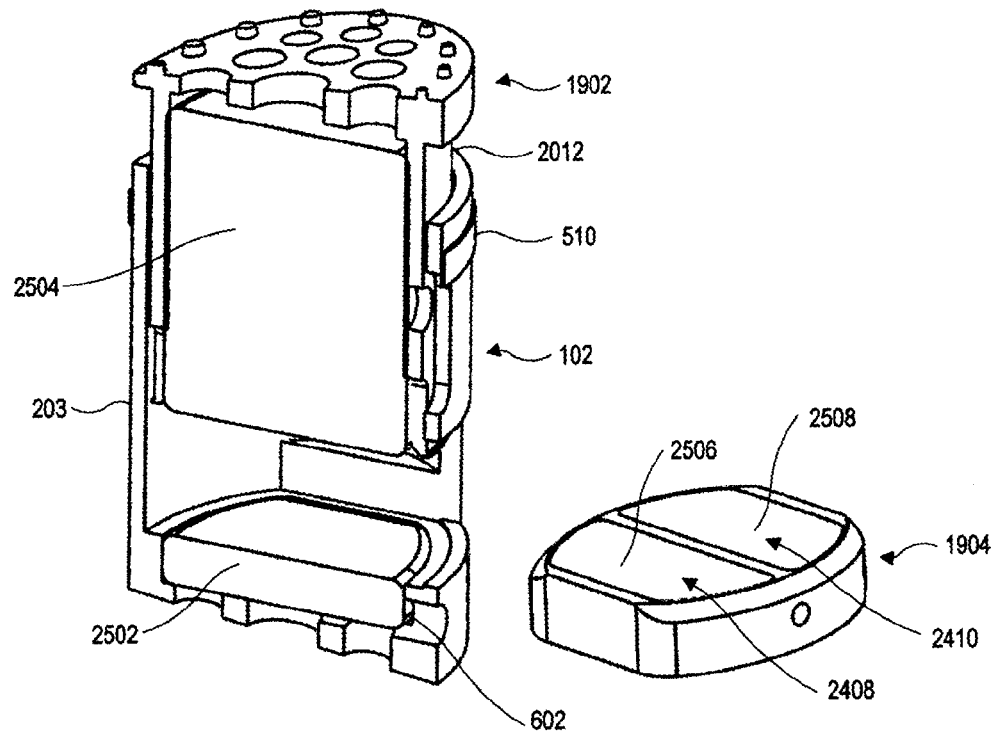
FIG. 25 illustrates a cross-sectional view of the corpectomy device of FIG. 19 that is pre-packed with grafting material.

FIG. 25 illustrates a cross-sectional view of an example corpectomy device 1900 of FIG. 19 that is pre-packed with grafting material. The corpectomy device 1900 has been expanded slightly from its collapsed state to illustrate the pre-packing of the corpectomy device 1900 in greater detail.

As illustrated, opening 602 of the outer component 102 is pre-packed substantially with grafting material 2502. The entire tubular body 2012 of the inner component 1902 is pre-packed substantially with grafting material 2504. Openings 2408, 2410 of the riser 1904 are pre-packed substantially with respective grafting material 2506, 2508.

It is noted that the pre-packed corpectomy device 1900 in its collapsed state (inner component 1902 fully inserted into outer component 102) is implanted into the defect site of the spinal column, then distracted sufficiently to receive the pre-packed riser 1904 into the outer component 102, and locked in its expanded state by the inner component 1902 engaging the riser 1904 and the outer component 102 as the distraction is released.

Figure 26:
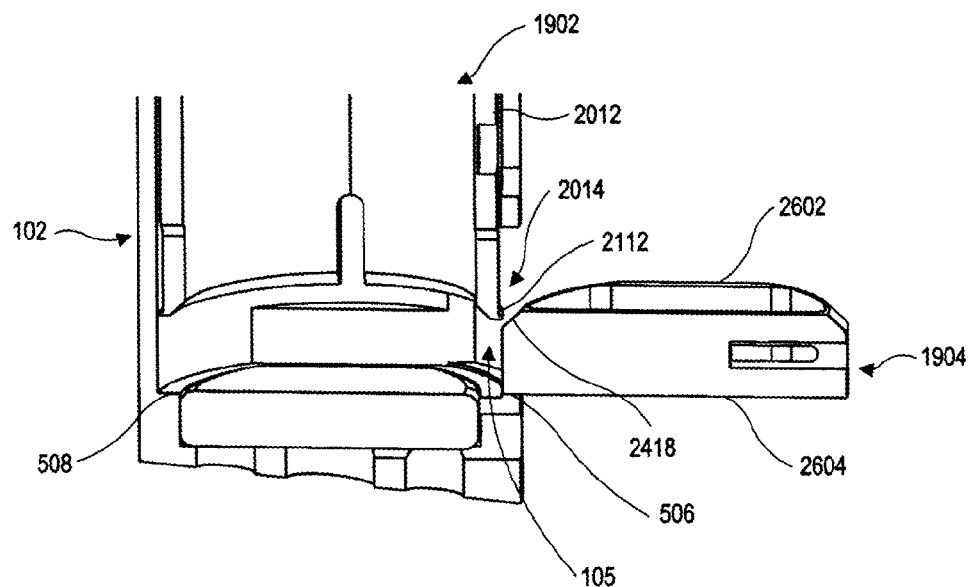
FIGS. 26 and 27 illustrate cross-sectional views of the corpectomy device of FIG. 19 to show in greater detail the insertion of the riser into the outer component to extend the corpectomy device from the collapsed state into the expanded state.
Figure 27:
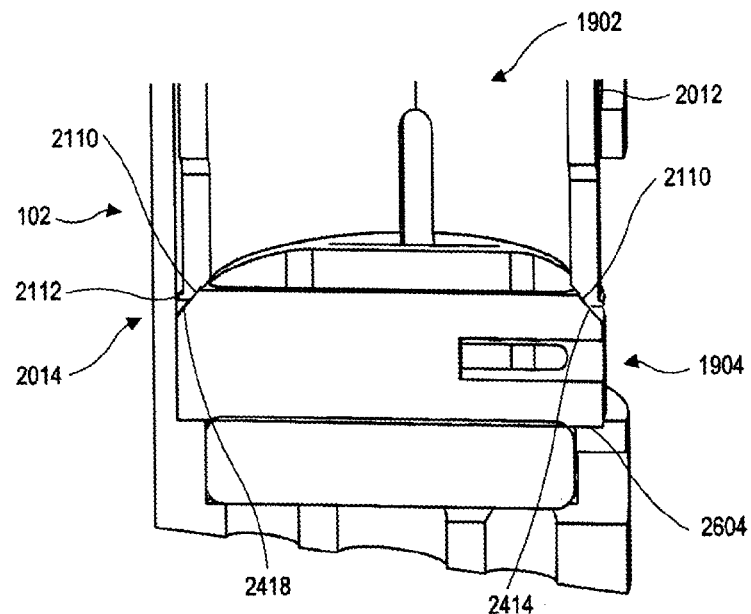

FIGS. 26 and 27 illustrate cross-sectional views of the corpectomy device 1900 to show in greater detail the insertion of the riser 1904 into the outer component 102 to extend the corpectomy device 1900 from a collapsed state to an expanded state. For purposes of clear illustration, some of the grafting material 2504-2508 of the respective components 1902, 1904 in the corpectomy device 1900 has been removed. It is noted, however, that a pre-packed corpectomy device 1900 illustrated in FIG. 25 will be used for spinal fusion procedures.

At this point it is assumed that the pre-packed components 102, 1902 of the corpectomy device 1900 in a collapsed state have been inserted into desired position in the defect site of the spinal column, with the endplates 202, 2002 of the components 102, 1902 contacting but not yet engaging the vertebrae of the defect site via respective attachment devices 208, 2010.

As illustrated in FIG. 26, the inner component 1902 has been distracted sufficiently with respect to outer component 102 from the collapsed state to open at least a portion of the window 105 in the outer component 102 in order to receive the riser 1904. In this state, the attachment devices 208, 2010 of the respective endplates 202, 2002 in the components 102, 1902 engage the vertebrae of the defect site. The riser 1904 is inserted through the window 105 into the seat 508 of the component 102.

To facilitate insertion of the riser 1904, the engagement member 2112 of the locking mechanism 2014 can ride the sloped surfaced 2418 and along a top surface 2602 of the riser 1904. Similarly, the ridge 506 and seat 508 can ride along a bottom surface 2604 of the riser 1904. As the engagement member 2112 clears the sloped surfaced 2418, the engagement member levels off along the top surface 2602 of the riser 1904 as the riser 1904 is inserted farther into the outer component 102.

Figure 28:
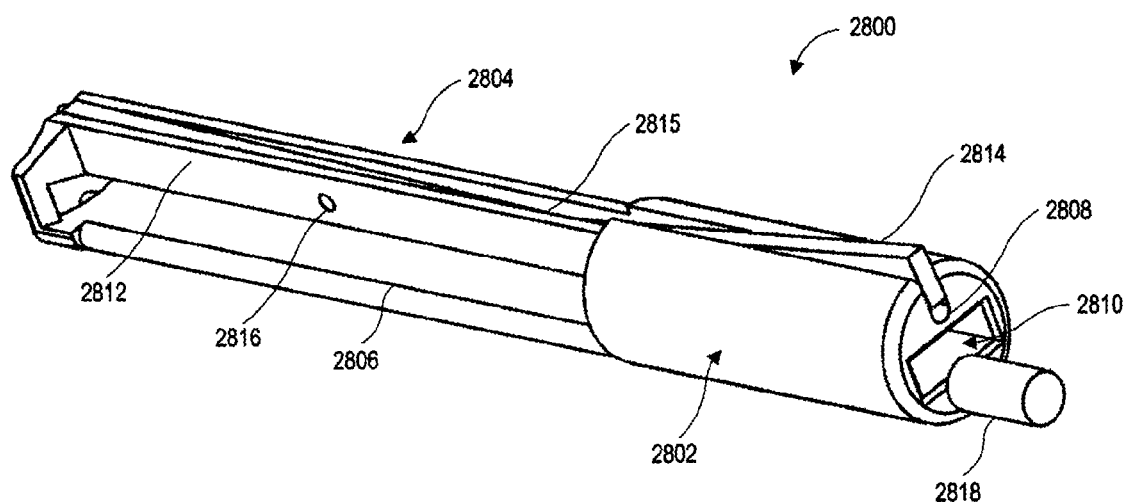
FIG. 28 illustrates a perspective view of an example inserter that is configured to insert the corpectomy device of FIGS. 1 and 19 into a defect site of a spinal column and to distract the corpectomy device in the defect site.

As further illustrated in FIG. 28, when the riser 1904 is fully inserted into the seat 508 of the outer component 102 such that the chamfered surface 2110 contacts the sloped surfaces 2414, 2418, the distraction with respect to components 102, 1902 is released. As the distraction is released, the vertebrae of the defect site apply a load to the corpectomy device 1900. The chamfered surface 2110 engages the sloped surfaces 2414, 2418 of the riser 1904, causing the tubular body 2012 of the inner component 1902 to expand circumferentially via the expansion slots 2108. The expansion of tubular body 2012 engages the engagement member 2112 of the inner component 1902 against the outer component 102.

The seat 508 of outer component 102 engages the bottom surface 2604 of the riser 1904. Accordingly, the riser 1904 is locked via the ridge 506 and locking mechanism 2014 in the outer component 102 by the inner component 1902. As illustrated in and described with reference to FIGS. 25-27, the corpectomy device 1900 has been extended from the collapsed (insertion) state into the expanded (operational) state. In the expanded state, the attachment devices 208, 2010 of the respective endplates 202, 2002 in the components 102, 1902 continue to engage the vertebrae of the defect site.

In the expanded state, the corpectomy device 1900 is under operational (load-bearing) conditions within the defect site of the spinal column. The engagement of the respective components 102, 1902, 1904 causes their pre-packed grafting material 2502-2508 to be in communication throughout the corpectomy device 100. Further, the pressure generated by the vertebrae (e.g., via ligaments, muscles) on the corpectomy device 1900 pressurizes the pre-packed grafting material 2502-2508 throughout the corpectomy device 1900. The communication and pressurization of the pre-packed grafting material 1402-1408 improves formation of the bridging bone though the corpectomy device 1900 and to the vertebrae of the defect site.

FIG. 28 illustrates a perspective view of an example inserter 2800 that is configured to insert the corpectomy device 100, 1900 into a defect site of the spinal column and to distract the corpectomy device 100, 1900 in the defect site. The inserter 2800 includes a handle 2802, extension member 2804, insertion surface 2806, channel 2808 and fixation mechanism 2818.

The handle 2802 is configured to allow the handling of the corpectomy device 100, 1900. The handle 2802 includes a window 2810 that is configured to allow the riser 106, 1904 to be communicated or introduced through the handle 2802 and extension member 2804 into the corpectomy device 100, 1900, as will be described in greater detail with reference to FIG. 30. The window 2810 generally approximates the dimensions of the window 105 of outer component 102 in the corpectomy device 100, 1900.

The extension member 2804 extends from the handle 2802 and is configured to interface with the corpectomy device 100, 1900 to enable insertion and distraction of the corpectomy device 100, 1900 in the defect site, as well as the introduction of the riser 106, 1904 into the corpectomy device 100, 1900 while in the defect site. The extension member 2804 includes a fixed arm component 2812 and a movable arm 2814.

The fixed arm component 2812 is configured to engage the opening 306 of the outer component 102 in the corpectomy device 100, 1900, as will be described in greater detail with reference to FIG. 29. The movable arm 2814 is pivotally secured to the fixed arm component 2812 at location 2816 (approximately midway along the fixed arm component) within channel 2808 and configured to pivot in relation to the fixed arm component 2812 at 2816. In some embodiments, the movable arm 2814 includes a bend at location 2815 that is displaced from location 2816, facilitating distraction of the corpectomy device 100, 1900. The movable arm 2814 is configured to extend through the opening 304 of the outer component 102 and to engage the opening 904, 2104 of the inner component 104, 1902 in the corpectomy device 100, 1900, as will be described in greater detail with reference to FIG. 29. Upon depressing the movable arm 2814 against the handle 2802, the corpectomy device 100, 1900 can be distracted to open the opening 105 in the outer component 102 to allow insertion of the riser 106, 1904 into the seat 508 of the outer component 102.

The insertion surface 2806 extends from the opening 2810 of the handle 2802 through the end of the extension member 2804. The insertion surface 2806 is configured to allow the riser 106, 1904 to be communicated or inserted through the handle 2802 and extension member 2804 into the corpectomy device 100, 1900, as will be described in greater detail with reference to FIG. 30.

The channel 2808 extends along the handle 2802 and the extension member 2804. The channel 2808 and bend in the movable arm 2814 are configured to provide a low profile extension member 2804 that allows sufficient pivoting of the movable arm 2814 with respect to the fixed arm component 2812 for distraction such that the movable arm 2814 remains mostly in the channel 2808, mitigating contact with structures outside the surgical corridor to the defect site.

The fixation mechanism 2818 is configured to secure the movable arm 2814 with respect to the fixed arm component 2812 in one or more fixed relationships to facilitate insertion of the riser 106, 1904 into the opening 105 of the outer component 102. In some embodiments, rotation of the fixation mechanism 2818 (clockwise and counterclockwise) can fixate and release fixation of the movable arm 2814 with respect to the fixed arm component 2812. In other embodiments, depression of the fixation mechanism 2818 can fixate the movable arm 2814 with respect to the fixed arm component 2812 and extension of the fixation mechanism 2818 can release the fixation of the movable arm 2814 with respect to the fixed arm component 2812.

Figure 29:
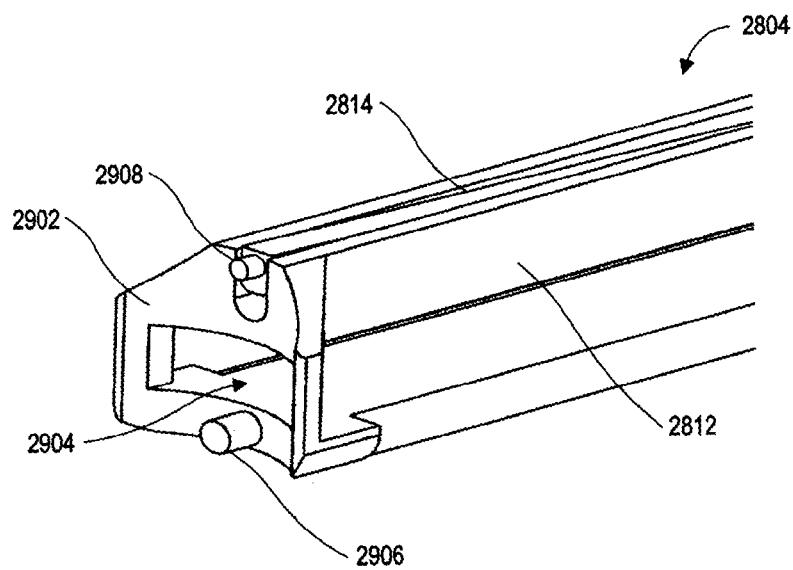
FIG. 29 illustrates a perspective view of the extension member of the inserter in FIG. 28.

FIG. 29 illustrates a perspective view of the extension member 2804 of the inserter 2800 illustrated in FIG. 28. The fixed arm component 2812 of the extension member 2804 further includes an interface 2902, window 2904 and extension 2906.

The interface 2902 is configured to engage the outer component 102 of the corpectomy device 100, 1900. The interface 2902 is arcuate (e.g., circular, oval or another shape) to engage the outer component 102 in a planar configuration about its circumference.

The window 2904 is configured to allow the riser 106, 1904 to be communicated or introduced through into the corpectomy device 100, 1900. The window 2904 approximates the dimensions of the window 105 of outer component 102 in the corpectomy device 100, 1900.

The extension 2906 is configured to engage the opening 306 of the outer component 102 in the corpectomy device 100, 1900.

The movable arm 2814 of the extension member 2804 includes an extension member 2908 configured to extend through opening 304 of the outer component 102 and to engage opening 904, 2104 of the inner component 104, 1902 in the corpectomy device 100, 1900.

Figure 30:
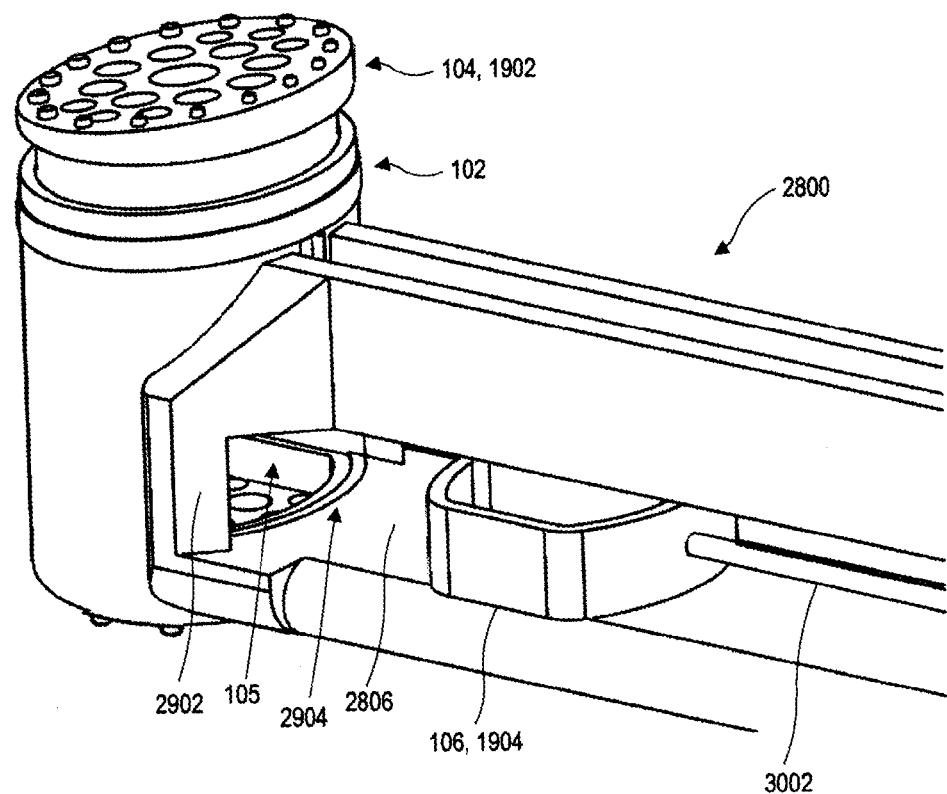
FIG. 30 illustrates a perspective view of introducing the corpectomy device of FIGS. 1 and 19 into a defect site of a spinal column and inserting the riser of FIGS. 1 and 19 into the corpectomy device.

FIG. 30 illustrates a perspective view of inserting the corpectomy device 100, 1900 into a defect site of a spinal column and introducing the riser 106, 1904 into the corpectomy device 100, 1900.

Initially, the corpectomy device 100, 1900 (outer component 102, inner component 104, 1902, riser 106, 1904) is pre-packed with grafting material as described herein. The corpectomy device 100, 1900 is assembled into its collapsed state (inner component 104, 1902 inserted into outer component 102; riser 106, 1904 being separate).

The extensions 2906, 2908 of the inserter 2800 are used to engage the openings 306, 904 or 2104 of the components 102, 104 or 1902. The inserter 2800 is used to insert the corpectomy device 100, 1900 in its collapsed state into the defect site of the spinal column. The corpectomy device 100, 1900 can be positioned in the defect site as required.

After insertion, the corpectomy device 100, 1900 is distracted by depressing the movable arm 2814 against the handle 2802 of the inserter 2800 to open the window 105 sufficiently to receive the riser 106, 1904 into the seat 508 of the outer component 102. Fixation mechanism 2818 can be used to fixate the movable arm 2814 with respect to the fixed arm component 2812 in a fixed pivotal relationship to maintain the window 105 open.

An introducer tool 3002 that includes an extension (not shown) is used to engage opening 1216, 2420 of the riser 106, 1904. The introducer tool 3002 is then used to introduce the riser 106, 1904 into the seat 508 of the outer component 102 along the surface 2806 through openings 2810, 2904 and 105.

After insertion of the riser 106, 1904 into the outer component 102, the fixation mechanism 2818 can be released causing the corpectomy device 100, 1900 to settle into the expanded state (operational load-bearing state), locking the riser 106, 1904 in the outer component 102 as described hereinabove. The introducer tool 3002 and then the inserter 2800 are removed from the corpectomy device 100, 1900 and withdrawn from the defect site of the spinal column. The pre-packed corpectomy device 100, 1900 remains in the defect site in its operational load-bearing state, causing formation of bone (fusion) between the vertebrae of the defect site and through the corpectomy device 100, 1900.

Thus, a pre-packed corpectomy device and method of bridging vertebrae with the corpectomy device to improve fusion have been described. Although specific example embodiments have been described, it will be evident that various modifications and changes can be made to these embodiments without departing from the broader scope of this application. Accordingly, the specification and drawings are to be regarded in an illustrative rather than a restrictive sense. The accompanying drawings that form a part hereof, show by way of illustration, and not of limitation, specific embodiments in which the subject matter can be practiced. The embodiments illustrated are described in sufficient detail to enable those skilled in the art to practice the teachings disclosed herein. Other embodiments can be utilized and derived therefrom, such that structural substitutions and changes can be made without departing from the scope of this application. This Detailed Description, therefore, is not to be taken in a limiting sense, and the scope of various embodiments is defined only by the appended claims, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention, inventive concept or embodiment. Thus, although specific embodiments have been illustrated and described herein, it should be appreciated that any arrangement calculated to achieve the same purpose can be substituted for the specific embodiments shown. This application is intended to cover any and all adaptations or variations of various embodiments. Combinations of the above embodiments and other embodiments not specifically described herein, will be apparent to those of skill in the art upon reviewing the above description.

The Abstract is provided to comply with 37 C.F.R. §1.72(b) and will allow the reader to quickly ascertain the nature of the technical disclosure of this application. It is submitted with the understanding that it will not be used to interpret or limit the scope or meaning of the claims.

In the foregoing description of the embodiments, various features can be grouped together in a single embodiment for the purpose of streamlining the disclosure of this application. This method of disclosure is not to be interpreted as reflecting that the claimed embodiments have more features than are expressly recited in each claim. Rather, as the following claims reflect, inventive subject matter lies in less than all features of a single disclosed embodiment.

What is claimed is:

1. A corpectomy device comprising:
    an outer component including a first endplate and a first tubular structure extending from the first endplate, the first tubular structure including an open top and a window extending through at least a portion of an outer boundary of the first tubular structure, the first tubular structure including a seat above the first endplate in communication with the window, the seat defining an opening that is configured to be pre-packed substantially with first grafting material;
    an inner component including a second endplate and a second tubular structure extending from the second endplate, the second tubular structure at least partially disposed in the first tubular structure such that the inner component is in a first telescoping configuration with respect to the outer component, the second tubular structure configured to be pre-packed substantially with second grafting material, the second tubular structure including a locking mechanism, wherein the locking mechanism includes a chamfered inner surface extending around an inner circumference of the second tubular structure towards the outside the second tubular structure, at least one expansion slot extending along the second tubular structure from the chamfered inner surface towards the second endplate, and an engagement member extending around an outer circumference of the second tubular structure; and
    a riser including a third tubular structure, the third tubular structure including a pair of opposing planar walls that intersect a pair of arcuate walls, wherein the pair of arcuate walls includes top sloping surfaces that extend down towards the outside of the riser, the riser configured to be received through the window into the seat of the first tubular structure such that the third tubular structure engages at least a portion of the second tubular structure and supports the inner component in a second telescoping configuration with respect to the outer component, the third tubular structure configured to be pre-packed substantially with third grafting material, the first grafting material, the second grafting material and the third grafting material to remain pre-packed substantially and in communication in the second telescoping configuration, wherein the locking mechanism secures the riser in the seat such that the chamfered inner surface engages the top sloping surfaces, the second tubular structure expands circumferentially via the at least one expansion slot when the chamfered inner surface engages the top sloping surfaces, and the engagement member engages the first tubular structure when the second tubular structure expands circumferentially.

2. The corpectomy device of claim 1, wherein the third tubular structure includes a middle planar wall extending approximately parallel to the opposing planar walls, the middle planar wall dividing the third tubular structure into a pair of openings, a first of the openings configured to be pre-packed substantially with a first portion of the third grafting material and a second of the openings configured to be pre-packed substantially with a second portion of the third grafting material.

3. The corpectomy device of claim 2, wherein the third tubular structure includes a pair of retention ridges disposed along lower portions of the openings, a first of the retention ridges configured to retain the first portion of the third grafting material in the first of the openings and a second of the retention ridges configured to retain the second portion of the third grafting material in the second of the openings.

4. The corpectomy device of claim 3, wherein the first of the retention ridges is disposed in the first of the openings along a lower portion of the middle planar wall.

5. The corpectomy device of claim 3, wherein the second of the retention ridges is disposed in the second of the openings along a lower portion of the middle planar wall.

6. The corpectomy device of claim 2, wherein the middle wall includes a locking mechanism configured to secure the riser in the seat by engaging the second tubular structure of the inner component.

7. The corpectomy device of claim 1, wherein the first endplate includes at least one opening that is in communication with the opening defined by the seat.

8. The corpectomy device of claim 7, wherein the at least one opening includes a first central opening, a plurality of second openings about the first central opening, and a plurality of third openings about the second openings.

9. The corpectomy device of claim 1, wherein the second endplate includes at least one opening that is in communication with an opening defined by the second tubular structure.

10. The corpectomy device of claim 9, wherein the at least one opening includes a first central opening, a plurality of second openings about the first central opening, and a plurality of third openings about the second openings.

11. The corpectomy device of claim 1, wherein first endplate provides between about a zero (0) and about a six (6) degree angle with respect to a horizontal plane through the corpectomy device.

12. The corpectomy device of claim 1, wherein second endplate provides between about a zero (0) and about a six (6) degree angle with respect to a horizontal plane through the corpectomy device.

13. The corpectomy device of claim 1, wherein first endplate and the second endplate provide between about a zero (0) and about a twelve (12) degree combined angle with respect to a horizontal plane through the corpectomy device.

14. The corpectomy device of claim 1, wherein first endplate and the second endplate provide between about a three (3) and about a nine (9) degree combined angle with respect to a horizontal plane through the corpectomy device.

15. The corpectomy device of claim 1, wherein the corpectomy device further comprises at least one reinforcement band disposed about a circumference of the first tubular structure.

16. The corpectomy device of claim 1, wherein the corpectomy device further includes a pair of opposing guide walls that intersect the seat and extend from the window into the first tubular structure, the guide walls configured to guide the riser into the seat.

17. The corpectomy device of claim 1, wherein the seat is recessed in the first tubular structure with respect to the window to provide a ridge that extends above the seat.

18. The corpectomy device of claim 1, wherein the seat includes a pair of opposing planar walls that extend from the window into the first tubular structure and a pair of opposing arcuate walls that intersect the opposing planar walls.

19. A corpectomy system comprising:
a corpectomy device comprising:
an outer component including a first endplate and a first tubular structure extending from the first endplate, the first tubular structure including an open top and a window extending through at least a portion of an outer boundary of the first tubular structure, the first tubular structure including a seat above the first endplate in communication with the window, the seat defining an opening that is configured to be pre-packed substantially with first grafting material, wherein the outer component further includes a first slot and a first engagement opening;
an inner component including a second endplate and a second tubular structure extending from the second endplate, the second tubular structure disposed in the first tubular structure such that the inner component is in a first telescoping configuration with respect to the outer component, the second tubular structure configured to be pre-packed substantially with second grafting material, wherein the inner component further includes a second engagement opening; and
a riser including a third tubular structure which has a configuration that approximates the second tubular structure, the riser configured to be received through the window into the seat of the first tubular structure such that the third tubular structure engages at least a portion of the second tubular structure and supports the inner component in a second telescoping configuration with respect to the outer component, the third tubular structure configured to be pre-packed substantially with third grafting material, the first grafting material, the second grafting material and the third grafting material to remain pre-packed substantially and in communication in the second telescoping configuration; and
an inserter tool configured to distract the inner component with respect to the outer component and to allow introduction of the riser into the seat of the outer component, wherein the inserter tool includes a first arm component and second arm pivotally connected to the first arm component, the first arm component including a first extension configured to removably engage the first engagement opening, the second arm including a second extension configured to extend through the first slot and to removably engage the second opening.

20. The corpectomy system of claim 19, wherein the inserter tool further includes a first terminal opening, a second terminal opening, and an insertion surface between the first terminal opening and the second terminal opening configured to communicate the riser through the inserter tool into the seat of the first tubular structure.

21. The corpectomy system claim 20, wherein the corpectomy system further comprises an introducer configured to introduce the riser through the first terminal opening and the second terminal opening via the insertion surface into the seat of the first tubular structure.

22. The corpectomy system claim 19, wherein the inserter tool further includes a fixation mechanism configured to fixate the first arm component in a fixed pivotal configuration with respect the second arm.

* * * * *